US009101567B2

(12) United States Patent
Huang et al.

(10) Patent No.: US 9,101,567 B2
(45) Date of Patent: *Aug. 11, 2015

(54) SUPPRESSION OF CANCER GROWTH AND METASTASIS USING NORDIHYDROGUAIARETIC ACID DERIVATIVES WITH 7-HYDROXYSTAUROSPORINE

(75) Inventors: Ru Chih C. Huang, Baltimore, MD (US); Kotohiko Kimura, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 91 days.

This patent is subject to a terminal disclaimer.

(21) Appl. No.: 13/579,953

(22) PCT Filed: Feb. 22, 2011

(86) PCT No.: PCT/US2011/025752
§ 371 (c)(1),
(2), (4) Date: Nov. 6, 2012

(87) PCT Pub. No.: WO2011/103586
PCT Pub. Date: Aug. 25, 2011

(65) Prior Publication Data
US 2013/0053335 A1 Feb. 28, 2013

Related U.S. Application Data

(60) Provisional application No. 61/306,680, filed on Feb. 22, 2010.

(51) Int. Cl.
| *A61K 31/09* | (2006.01) |
| *A61K 31/553* | (2006.01) |
| *A61K 31/7028* | (2006.01) |
| *A61K 31/075* | (2006.01) |
| *A61K 31/198* | (2006.01) |
| *A61K 31/225* | (2006.01) |
| *A61K 31/401* | (2006.01) |
| *A61K 31/417* | (2006.01) |
| *A61K 45/06* | (2006.01) |

(52) U.S. Cl.
CPC ............... *A61K 31/09* (2013.01); *A61K 31/553* (2013.01); *A61K 31/7028* (2013.01); *A61K 31/075* (2013.01); *A61K 31/198* (2013.01); *A61K 31/225* (2013.01); *A61K 31/401* (2013.01); *A61K 31/417* (2013.01); *A61K 45/06* (2013.01)

(58) Field of Classification Search
None
See application file for complete search history.

(56) References Cited

U.S. PATENT DOCUMENTS

| 4,935,415 | A | * | 6/1990 | Nakano et al. | ........... 514/211.08 |
| 5,541,232 | A | | 7/1996 | Howell et al. | |
| 6,214,821 | B1 | * | 4/2001 | Daoud | ..................... 514/214.02 |
| 6,806,266 | B1 | | 10/2004 | Kanai et al. | |
| 2007/0134758 | A1 | * | 6/2007 | Planelles et al. | ............. 435/69.1 |
| 2008/0207532 | A1 | | 8/2008 | Huang et al. | |

FOREIGN PATENT DOCUMENTS

| JP | 07224067 | 8/1995 |
| WO | 2009089366 A2 | 7/2009 |

OTHER PUBLICATIONS

Lambert, J., Dorr, R., & Timmermann, B. (2004). Nordihydroguaiaretic acid: a review of its numerous and varied biological activities. Pharmaceutical biology, 42(2), 149-158.*
Hare, T., et al., "Suppression of basal autophagy in neural cells causes neurodegenerative disease in mice" Nature 441: 885-9. (2006).
Karantza-Wadsworth, V., et al., "Autophagy mitigates metabolic stress and genome damage in mammary tumorigenesis" Genes Dev. 21: 1621-35. (2007).
Komatsu, M., et al., "Loss of autophagy in the central nervous system causes neurodegeneration in mice" Nature 441: 880-4. (2006).
Komatsu, M., et al., "Homeostatic levels of p62 control cytoplasmic inclusion body formation in autophagy-deficient mice" Cell 131: 1149-11b3. (2007).
Kuma, A., et al., "The role of autophagy during the early neonatal starvation period" Nature 432: 1032-6. (2004).
Lum, J., et al., "Growth factor regulation of autophagy and cell survival in the absence of apoptosis" Cell 120: 237-48. (2005).
Mathew, R., et al., "Autophagy suppresses tumor progression by limiting chromosomal instability" Genes Dev. 21: 1367-81. (2007).
Levine, B, et al., "Autophagy in the pathogenesis of disease" Cell 132: 27-42. (2008).
Mathew, R, et al., "Role of autophagy in cancer" Nat. Rev. Cancer 7: 961-7. (2007).
Lopez, R., et al., "The anticancer activity of the transcription inhibitor terameprocol (meso-tetra-O-methyl nordihydroguaiaretic acid) formulated for systemic administration" Anti-Cancer Drugs 18:933-939. (2007).
Akinaga, S., et al., "UCN-01 (7-hydroxystaurosporine) and other indolocarbazole compounds: a new generation of anti-cancer agents for the new century?" Anticancer Drug Des. 15:43-52. (2000).
Rubinsztein, D., et al., "In search of an autophagomometer" Autophagy 5: 585-589. (2009).
Amaravadi, R, et al., "Autophagy inhibition enhances therapy-induced apoptosis in a Myc-induced model of lymphoma" J. Clin. Invest. 117:326-336. (2007).
Ding, W., et al., "Differential Effects of Endoplasmic Reticulum Stress-induced Autophagy on Cell Survival" J. Biol. Chem. 282: 4702-10. (2007).
Tracy, K., et al., "BIVIP3 Is an RBIE2F Target Gene Required for Hypoxia-Induced Autophagy" Mol. Cell, Biol. 27: 6229-42 (2007).

(Continued)

*Primary Examiner* — Shaojia Anna Jiang
*Assistant Examiner* — Dale R Miller
(74) *Attorney, Agent, or Firm* — Johns Hopkins Technology Transfer

(57) ABSTRACT

Disclosed is a composition comprising a derivative of NDGA and 7-hydroxystaurosporine. The composition can be in a unit dose form or kit. Also disclosed are methods for achieving cytotoxicity, particularly of rapidly dividing cells such as cancer, by administering a composition of the invention. In various embodiments of the invention subjects with cancer achieve prolonged survival and/or diminution in the size of their malignancies and cancer metastasis.

11 Claims, 14 Drawing Sheets

(56) References Cited

OTHER PUBLICATIONS

Eads, D., et al., "Terameprocol, a methylated derivative of nordihydroguaiaretic acid, inhibits production of prostaglandins and several key inflammatory cytokines and chemokines" J. Inflamm. 6: 2-19. (2009).

Shaw, J., et al., "Antagonism of E2F-1 regulated Bnip3 transcription by NF-xB is essential for basal cell survival" Proc. Nat. Acad. Sci. USA. 105: 20734-9. (2008).

Shaw, J., et al., "Transcriptional silencing of the death gene BNIP3 by cooperative action of NF-kB and histone deacetylase 1 in ventricular myocytes" Circ. Res. 99: 1347-54. (2006).

Lamkanfi, N., et al., "Targeted peptidecentric proteomics reveals caspase-7 as a substrate of caspase-1 inflammasomes" Mol, Cell. Proteomics 7: 2350-63. (2008).

Gafni, J., et al., "Calpain-1 cleaves and activates caspase-7" Biol. Chem. 284: 25441-9. (2009).

Mazcelli, M., et al., "Caspase-7 is activated during lovastatin-induced apoptosis of the prostate cancer cell line LNCaP" Cancer Res. 58: 76-83. (1998).

Rokhlin, O., et al., "Fas-mediated apoptosis in human prostatic carcinoma cell lines occurs via activation of caspase-8 and caspase-7" Cancer Res. 15 58:5870-5. (1998).

Kroemer, G., et al., Caspase-independent cell death. Nature Med.11 : 725-30. (2005).

Wu, Y., et al., "Autophagy plays a protective role during zVAD-induced necrotic cell death" Autophagy 4: 457-66. (2008).

Omuro, A., "Exploring multi-targeting strategies for the treatment of gliomas" Current Opinion in Investigational Drugs, vol. 9, No. 12, pp. 1287-1295 (2008).

Akinaga, S. et al., "Enhancement of antitumor activity of mitomycin C in vitro and in vivo by UCN-01, a selective inhibitor of protein kinase C", Cancer Chemother Pharmacol, vol. 33, pp. 183-189 (1993).

Henry, P., et al., "Inhibitory effects of nordihydroguaiaretic acid on ETA-receptor-mediated contractions to endothelin-I in rat trachea." Br J pharmacol., vol. 111, pp. 561-569 (1994).

Hwu, J. et al. Antiviral activities of methylated nordihydrvguaiaretic acids. 1. Synthesis, structure identification, and inhibition of tat-regulated HN transactivation. J. Med. Chem. 41:2994-3000. (1998).

Chen, H., et al., "Antiviral activities of methylated nordihydroguaiaretic acids. 2. Targeting herpes simplex virus replication by the mutation insensitive transcription inhibitor tetra-Omethyl-NDGA", J. Med. Chem. 41;3001-3007. (1998).

Heller, J., et al., "Tetra-O-methyl nordihydroguaiaretic acid induces G2 arrest in mammary cells and exhibits tumoricidal activity in vivo", (2001) Cancer Res. 61;5499-5504.

Chang, C., et al., "Tetra-O-methyl nordihydraguaiaretic acid induces growth arrest and cellular apoptosis by inhibiting Cdc2 and surviving expression", (2004) Proc. Natl. Acad. Sci. U.S.A. 101:13239-13244.

Park, R., et al., "Systemic treatment with tetra-O-methyl nordihydroguaiaretic acid suppresses the growth of human xenograft tumors", (2005) Clin. Cancer Res. 11:4601-4609.

Wang, L., et al., "Transcription factor Spl expression is a significant predictor of survival in human gastric cancer", (2003) Clin. Cancer Res. 9: 6371-80.

Yao, J., et al., "Association between expression of transcription factor Spl and increased vascular endothelial growth factor", (2004) Clin. Cancer Res. 10: 4109-17.

The data from a clinical trial: Study of Intralesional Injection of M4N in Patients with Refractory Malignant Tumors of the Head and Neck. ClinicalTrials.gov identifier: NCT00057512, (http://clinicaltrials.gov/ct2/show/NCT00057512?term=em1421&rank=6) (2003).

N. Khanna, R., et al., "Phase I/II clinical safety studies of terameprocol vaginal ointment", (2007) Gynecologic Oncology 107: 554-562.

The data from a clinical trial: Tetra-O-methyl Nordihydroguaiaretic acid in treating patients with recurrent high-grade glioma. ClinicalTrials.gov identifier: NCT00404248, (http://clinicaltrials.gov/ct2/show/NCT00404248?term=M4N&rank=5) (2006).

Baxevanis, C., et al., "Combinatorial treatments including vaccines, chemotherapy and monoclonal antibodies for cancer therapy", Cancer Immunol Immunother. 5 8: 317-24. (2009).

Michelakis, E., et al., "Metabolic Modulation of Glioblastoma with Dichloroacetaye", Sci. Transl. Med. 2: 31-4. (2010).

Hockenbery, D., "Targeting mitochondria for cancer therapy", Environmental and Molecular Mutagenesis 51:476-489 (2010).

Garrido, C., et al., "Mechanisms of cytochrome c release from mitochondria" Cell Death Differ. 13: 1423-33. (2006).

Martinez-Caballero, S., et al., "The role of the mitochondrial apoptosis induced channel MAC in cytochrome c release" J. Bioenerg. Biomembr. 37: 155-64. (2005).

Tait, S., et al., "Mitochondria and cell death: outer membrane permeabilization and beyond", Nat. Rev. Mol. Cell. Biol. 11:621-32. (2010).

Leber, B., et al., "Drugs targeting Bcl-2 family members as an emerging strategy in cancer" Expert Rev. Mol. Med. 12:e28 (2010).

Kang, M., et al., "Bcl-2 inhibitors: targeting mitochondrial apoptotic pathways in cancer therapy" Clin. Cancer Res. 15: 1126-32 (2009).

Chonghalle, T., et al., "Mimicking the BH3 domain to kill cancer cells", Oncogene. Supple 1:5149-57 (2008).

Garcia-Saez, A., Permeabilization of the outer mitochondria) membrane by Bcl-2 proteins. Adv. Exp. Med. Biol. 677: 91-105 (2010).

Burton, T., "The role of Bcl-2 family member Br1IP3 in cell death and disease: NIPping at the heels of cell death" Cell Death Diff. 16:515-23. (2009).

Zhang, F., et al., Role of BNIP3 and TTIX in cell death, autophagy, and mitophagy. Cell Death Diff. 16: 939-46 (2009).

Zhang, H et al., Mitochondria Autophagy Is an HIF-1-dependent 20 Adaptive Metabolic Response to Hypoxia. J. Biol. Chem. 283:10892-903. (2008).

Kubli, D., et al., Bnip3 mediates mitochondria dysfunction and cell death through Bax and Bak. Biochem. J. 405: 407-15. (2007).

Quinsay, M., et al., Bnip3 mediates permeabilization of mitochondria and release of cytochrome c via a novel mechanism. J. Mol. Cell Cardiol. 48: 1146-56. (2010).

White, E., et al., The Double-Edged Sword of Autophagy Modulation in Cancer. Clin. Cancer Res. 15: 5308-16. (2009).

Maiuri, M., et al., Control of autophagy by oncogenes and tumor suppressor genes. Cell Death Diff.16:87-93. (2009).

Degenhardt, K., et al., Autophagy promotes tumor cell survival and restricts necrosis, inflammation, and tumorigenesis. Cancer Cell 10: 51-64. (2006).

* cited by examiner

SUPPRESSION OF CANCER GROWTH AND METASTASIS USING NORDIHYDROGUAIARETIC ACID DERIVATIVES WITH 7-HYDROXYSTAUROSPORINE

CROSS-REFERENCE TO RELATED APPLICATIONS

This application is a 35 U.S.C. 371 U.S. National Stage entry of International Application No. PCT/US2011/025752, having an international filing date of Feb. 22, 2011, and claims the benefit of U.S. Provisional Application No. 61/306,680, filed Feb. 22, 2010, the contents of both of which are incorporated herein by reference in their entireties.

FIELD OF THE INVENTION

This invention relates to the use of nordihydroguaiaretic acid derivatives together with 7-hydroxystaurosporine (UCN-01) to treat cancer, prevent metastasis, and prolong the life of a mammal afflicted with a tumor. The invention also relates to methods of using nordihydroguaiaretic acid derivatives as cellular protectants.

BACKGROUND

Carcinogenesis is a multistage event affected by a variety of genetic and epigenetic factors and is typified by the outbreak of uncontrolled cell growth originated from different tissues. A universal goal for anticancer research lies in the development of a clinical treatment that is highly effective in curtailment of tumor growth, non-toxic to the host, and is affordable for most patients. Drugs that inhibit targets that are unique to dividing cells, particularly cells dividing in an uncontrolled manner, are an ideal paradigm for chemotherapeutic agents, the greater the specificity to cells that are dividing in an uncontrolled manner the lower the risk of attendant side effects.

The inventors and colleagues have previously reported that the tetra-O-methyl nordihydroguaiaretic acid ($M_4N$), also known as EM1421 and terameprocol, a semi-chemically synthesized derivative of nordihydroguaiaretic acid (NDGA) possessed antiviral (1, 2) and anti-cancer (3) activities in cultured cells, in mouse models (3, 4), and in human xenografts in nude mice (5). As a transcription inhibitor, $M_4N$ suppresses Sp1-regulated cdk expression and causes cell cycle arrest at the G2 phase of the cell cycle (3, 4). The overexpression of Sp1 has been shown to have significant roles in development and progression of gastric cancer (6, 7). The safety and possible tumoricidal capability of $M_4N$ was examined for human patients either through intralesional (8) or topical applications (9). $M_4N$ currently undergoes Phase I/II clinical trials in patients by intravenous infusion (10). The clinical trial data so far indicated that $M_4N$ had substantial anticancer efficacy. However the data also suggested that it is desirable if we can find some ways to strengthen the anticancer activity of the drug since the tumoricidal efficacy of this drug is not strong enough in most of cases. There are many reports to indicate that the combination drug regimens based on several anticancer drugs are effective for the treatment of certain type of cancers (11, 12). In this study we explored possible anticancer combination drug treatments based on $M_4N$, and investigated mechanistic backgrounds for effective anticancer therapy. Inhibiting cell death is widely accepted as a necessary step in the transition from normal to cancer cells, and most cancer therapies exert their effects by indirectly reversing this process (13, 14). Mitochondria are known to be a key element in cell death mechanisms. The activation of Apaf-1, caspase-9 and -3, and ICAD (DFF45) by cytochrome c egress from mitochondria is considered to be the most important mechanism for apoptosis induction (15). Usually mitochondrial membrane potential depolarization accompanies activation of cell death signal in mitochondria (16, 17). In many cancer cells, mitochondrial membrane potential is hyperpolarized rather than depolarized, which is one of many indications implying that cell death mechanism at the mitochondrial level is often broken in cancer (13, 14). For this reason it is quite understandable why many efforts of anticancer drug development are focused on normalizing mitochondria-related cell death pathway (18-20). Bcl-2 family proteins which are either pro-apoptotic or anti-apoptotic regulate cell death at the mitochondrial level (21). BNIP-3 is a protein belonging to Bcl-2 family protein family. This protein is a pro-apoptotic protein which is considered to mediate cell death signal through mitochondria under the stress conditions, most notably under hypoxic condition. Since cancer cells are often exposed to hypoxic condition because tumors often don't get enough blood oxygen supply, the study on this particular protein is very important to understand pathology of cancer development and prevention.

In recent years many cancer researchers have investigated extensively about autophagy as well as cell death, considering the exploitation of both of these physiological mechanisms to be crucial for establishing effective anticancer therapeutic regimens (27, 28). In the literatures there is clear evidence from the phenotypes of mutant mice, and cells derived from the mice, that autophagy functions to sustain cell survival, particularly during stress (29-36). It is also clear that there is functional interaction between autophagy and cell death pathways (37, 38). In response to metabolic stress, autophagy can delay cell death by apoptosis, and in apoptotic-defective cells, inactivation of the autophagy survival pathway promotes necrotic cell death in vitro and in tumors in vivo (29, 31, 38). Considering this recent progress in cancer research, mechanistic perspectives of both cell death and autophagy will be addressed for establishing effective combination drug regimens based on M4N in this study.

This application claims priority to U.S. Provisional Patent Application 61/306,680, filed Feb. 22, 2010, which is incorporated by reference in its entirety.

SUMMARY

As set forth herein, $M_4N$ and related derivatives of nordihydroguaiaretic acid have been used in combination with 7-hydroxystaurosporine to produce excellent results in tumor treatment, including prolonged patient survival as well as cytotoxicity to malignant cells. Accordingly, it is one object to provide a pharmaceutical composition comprising an effective amount of nordihydroguaiaretic acid (NDGA) or a derivative thereof of formula I:

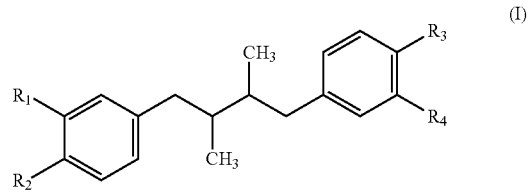

wherein $R_1$, $R_2$, $R_3$ and $R_4$ independently represent hydroxy, a straight or branched chain lower alkyl or alkoxy, an amino acid residue, a substituted amino acid residue, a nitrogen-containing 5- or 6-membered heterocyclic ring or a saccharide residue; the amino acid residue, substituted amino acid residue, nitrogen-containing 5 or 6 membered heterocyclic ring or saccharide residue being optionally joined to the phenyl ring by a linker of an oxygen atom and 1-10 carbon atoms, and an effective amount of 7-hydroxystaurosporine. In one specific embodiment, the pharmaceutical composition comprises the NDGA derivative tetra-o-methyl nordihydroguaiaretic acid ($M_4N$). In another specific embodiment, the pharmaceutical composition comprises the NDGA derivative maltose $M_3N$. In other specific embodiments, $R_1$, $R_2$, $R_3$ and $R_4$ are identical and represent straight or branched chain lower alkoxy groups or naturally occurring amino acid residues.

Also provided is a method of treating a tumor, comprising administering to a mammal in need of treatment an effective amount of the above-described pharmaceutical composition.

The mammal can be any mammal afflicted with a tumor amenable to treatment, for example a human, nonhuman primate, cat, dog, mouse, etc. The tumor may be a solid or hematological tumor, benign or malignant (metastatic or nonmetastatic), such as, for example, breast, liver, prostate, cervical, ovarian, colon, brain, pancreatic, bladder esophagus, gut, head and neck, kidney, melanoma, stomach, testes, thyroid, uterine and lung cancers, leukemias and lymphomas, such as acute myelogenous leukemia, acute or chronic lymphocytic leukemia, Hodgkin's and non-Hodgkin lymphoma, and myelomas. Persons of skill in the art will be able to determine by routine experimentation the types of tumors that are amenable to treatment. The treatment method is particularly suitable for treatment of metastatic and nonmetastatic cancer.

Also provided is a method of preventing or inhibiting tumor growth in an animal, said method comprising administering an effective amount of nordihydroguaiaretic acid (NDGA) or a derivative thereof of formula I:

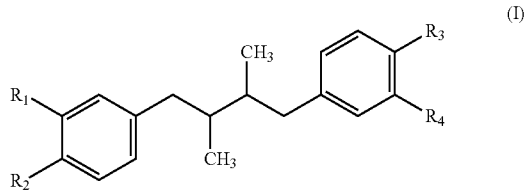

(I)

wherein $R_1$, $R_2$, $R_3$ and $R_4$ independently represent hydroxy, a straight or branched chain lower alkyl or alkoxy, an amino acid residue, a substituted amino acid residue, a nitrogen-containing 5- or 6-membered heterocyclic ring or a saccharide residue; the amino acid residue, substituted amino acid residue, nitrogen-containing 5 or 6 membered heterocyclic ring or saccharide residue being optionally joined to the phenyl ring by a linker of an oxygen atom and 1-10 carbon atoms, and an effective amount of 7-hydroxystaurosporine. In one specific embodiment, the NDGA derivative is tetra-o-methyl nordihydroguaiaretic acid ($M_4N$). In another specific embodiment, the NDGA derivative is maltose $M_3N$ (90). In other specific embodiments, $R_1$, $R_2$, $R_3$ and $R_4$ are identical and represent straight or branched chain lower alkoxy groups or naturally occurring amino acid residues.

The mammal can be any mammal afflicted with a tumor amenable to treatment, for example a human, nonhuman primate, cat, dog, mouse, etc.

The tumor may be a solid or hematological tumor, benign or malignant (metastatic or nonmetastatic), such as, for example, breast, prostate, cervical, ovarian, colon, brain, pancreatic and lung cancers, leukemias and lymphomas, and others mentioned hereinabove. Persons of skill in the art will be able to determine by routine experimentation the types of tumors that are amenable to treatment. The treatment method is particularly suitable for treatment of metastatic and nonmetastatic cancer.

Also provided is a method of preventing tumor metastasis in a mammal, said method comprising administering an effective amount of nordihydroguaiaretic acid (NDGA) or a derivative thereof of formula I:

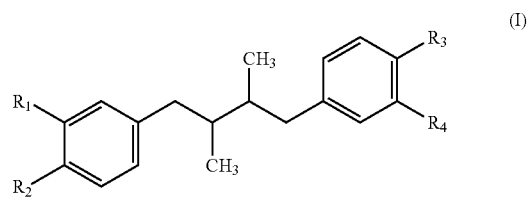

(I)

wherein $R_1$, $R_2$, $R_3$ and $R_4$ independently represent hydroxy, a straight or branched chain lower alkyl or alkoxy, an amino acid residue, a substituted amino acid residue and a saccharide residue; the amino acid residue, substituted amino acid residue or saccharide residue being optionally joined to the phenyl ring by a linker of an oxygen atom and 1-10 carbon atoms; and an effective amount of 7-hydroxystaurosporine.

In one specific embodiment, the NDGA derivative is tetra-o-methyl nordihydroguaiaretic acid ($M_4N$). In another specific embodiment, the NDGA derivative is maltose $M_3N$. In other specific embodiments, $R_1$, $R_2$, $R_3$ and $R_4$ are identical and represent straight or branched chain lower alkoxy groups or naturally occurring amino acid residues.

The mammal can be any mammal afflicted with a tumor amenable to treatment, for example a human, nonhuman primate, cat, dog, mouse, etc.

The tumor may be a solid or hematological tumor, such as, for example, breast, prostate, cervical, ovarian, colon, brain, pancreatic and lung cancers, leukemias and lymphomas, and others mentioned hereinabove. Persons of skill in the art will be able to determine by routine experimentation the types of tumors that are amenable to treatment. Treatment may be administered alone, or as an adjuvant to surgery, e.g. before surgery, for example, to reduce tumor size, and/or following surgery to reduce the possibility of metastases, e.g. by inhibition of the growth and migration of circulating tumor cells through the blood stream.

The invention also provides a method of prolonging the life of a mammal having a malignant tumor, said method comprising administering to the mammal an effective amount of nordihydroguaiaretic acid (NDGA) or a derivative thereof of formula I:

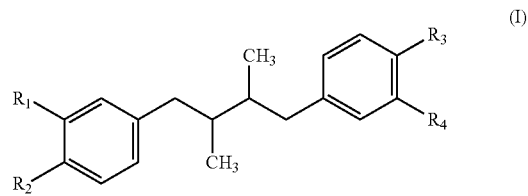

(I)

wherein $R_1$, $R_2$, $R_3$ and $R_4$ independently represent hydroxy, a straight or branched chain lower alkyl or alkoxy, an amino acid residue, a substituted amino acid residue and a saccharide residue; the amino acid residue, substituted amino acid residue or saccharide residue being optionally joined to the phenyl ring by a linker of an oxygen atom and 1-10 carbon atoms; and an effective amount of 7-hydroxystaurosporine.

In one specific embodiment, the NDGA derivative is tetra-o-methyl nordihydroguaiaretic acid ($M_4N$). In another specific embodiment, the NDGA derivative is maltose $M_3N$. In other specific embodiments, $R_1$, $R_2$, $R_3$ and $R_4$ are identical and represent straight or branched chain lower alkoxy groups or naturally occurring amino acid residues.

The mammal can be any mammal afflicted with a tumor amenable to treatment, for example a human, nonhuman primate, cat, dog, mouse, etc.

The tumor may be a solid or hematological tumor, such as, for example, breast, prostate, cervical, ovarian, colon, brain, pancreatic and lung cancers, leukemias and lymphomas, and other tumors mentioned hereinabove. Persons of skill in the art will be able to determine by routine experimentation the types of tumors that are amenable to treatment.

It has also been found, as detailed below, that $M_4N$ exerts a protective effect on normal cells in disease states, and is able to protect normal cells from otherwise toxic compounds during chemotherapy. Therefore, another aspect of the invention is a method of preventing caspase-dependent cell death in a subject afflicted with a disease or disorder, said method comprising the step of administering an effective amount of $M_4N$ to said subject. In one embodiment the disease or disorder is myocardial infarction. In another embodiment, the disease or disorder is cancer. In one specific embodiment, caspase dependent cell death caused by a chemotherapeutic agent is prevented by the administration of $M_4N$.

Formulations and Administration suitable for IV, IP, Topical and Oral Application.

Pharmaceutical compositions in accordance with the invention are useful for diagnosis, prognosis, prophylaxis or treatment of a condition. Accordingly, compositions in accordance with the invention are useful as a drug or as information for structural modification of existing compounds, e.g., by rational drug design. Compounds and methods of the invention are useful for screening compounds having an effect on a variety of conditions.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, intraperitoneally, intramuscular, or intradermal injections that provide continuous, sustained levels of the drug in the patient. Treatment of human patients or other animals are generally carried out using a therapeutically effective amount of a therapeutic of the invention in a physiologically-acceptable carrier. Suitable carriers and their formulation are described, for example, in Remington's Pharmaceutical Sciences by E. W. Martin.

The amount of the therapeutic agent to be administered varies depending upon the manner of administration, the age and body weight of the subject/patient, and with the subject's symptoms and condition. A compound is administered at a dosage that best achieves medical goals with the fewest corresponding side effects.

Administration

The pharmaceutical compositions of this invention including biologically active fragments, variants, or analogs thereof, can be administered by any suitable routes including intracranial, intracerebral, intraventricular, intrathecal, intraspinal, oral, topical, rectal, transdermal, subcutaneous, intravenous, intramuscular, intranasal, and the like. In one embodiment, the compositions are added to a retained physiological fluid, such as cerebrospinal fluid, blood, or synovial fluid. The compositions of the invention can be amenable to direct injection or infusion at a site of disease or injury.

Compositions for parenteral use may be provided in unit dosage forms (e.g., in single-dose ampules), or in vials containing several doses and in which a suitable preservative may be added. The composition may be in the form of a solution, a suspension, an emulsion, an infusion device, or a delivery device for implantation, or it may be presented as a dry powder to be reconstituted with water or another suitable vehicle before use. The composition may include suitable parenterally acceptable carriers and/or excipients.

In one approach, a therapeutic of the invention is provided within an implant, such as an osmotic pump, or in a graft comprising appropriately transformed cells. Methods of introduction may also be provided by rechargeable or biodegradable devices. Various slow release polymeric devices have been developed and tested for the controlled delivery of drugs, including proteinacious biopharmaceuticals. A variety of biocompatible polymers (including hydrogels), including both biodegradable and non-degradable polymers, can be used to form an implant for the sustained release of a bioactive factor at a particular target site.

Generally, the amount of administered agent of the invention (dosage) will be empirically determined in accordance with information and protocols known in the art. Typically agents are administered in the range of about 10 μg/kg to 100 mg/kg of the recipient. Other additives may be included, such as stabilizers, bactericides, and anti-fungals. These additives will be present in conventional amounts.

The administration of a compound of the invention may be by any suitable means that results in a concentration of the therapeutic that, combined with other components, is effective in ameliorating, reducing, or stabilizing a deficit or disorder. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Formulation of Pharmaceutical Compositions

As noted above, compositions of the invention can be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, cited herein.

For example, pharmaceutical compositions according to the invention may be in the form suitable for sterile injection. To prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate).

Suitable dosage forms can be formulated for, but are not limited to, oral, rectal, sub-lingual, mucosal, nasal, ophthalmic, subcutaneous, intramuscular, intravenous, transdermal, spinal, intrathecal, intra-articular, intra-arterial, subarachinoid, bronchial, lymphatic, and intra-uterille administration, and other dosage forms for systemic delivery of active ingredients. In a preferred embodiment, the dosage form is suitable for injection or intravenous administration.

To prepare such pharmaceutical dosage forms, one or more of the aforementioned compounds are intimately admixed with a pharmaceutical carrier according to conventional pharmaceutical compounding techniques. The carrier may take a wide variety of forms depending on the form of preparation desired for administration.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Methods in accordance with the present invention using formulations suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught.

Formulations for oral use include tablets containing active ingredient(s) of the invention in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

As appropriate, a tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

As appropriate, a syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration usually comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of the invention may further include one or more accessory ingredient(s) selected from diluents, buffers, flavoring agents, binders, disintegrants, surface active agents, thickeners, lubricants, preservatives (including antioxidants), and the like.

A formulation of the present invention can have immediate release, sustained release, delayed-onset release or any other release profile known to one skilled in the art. Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target the site of a pathology. For some applications, controlled release formulations obviate the need for frequent dosing to sustain the enzyme activity at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The compositions of the invention can be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Alternatively, the active drug may be incorporated in biocompatible carriers, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Salts and Derivatives

Compositions of the invention can comprise various pharmaceutically acceptable salts, ether derivatives, ester derivatives, acid derivatives, and aqueous solubility altering derivatives of the active compound. The present invention can comprise all individual enantiomers, diastereomers, racemates, and other isomer of compounds of the invention. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention. Prodrugs and active metabolites of compounds of the invention are also within the scope of the invention.

A prodrug is a pharmacologically inactive compound that is converted into a pharmacologically active agent by a metabolic transformation. In vivo, a prodrug is acted on by naturally occurring enzyme(s) resulting in liberation of the pharmacologically active agent. Conventional procedures for the selection and preparation of suitable prodrug derivatives are described, for example, in "Design of Prodrugs", ed. H. Bundgaard, Elsevier, 1985.

An active metabolite is a compound which results from metabolism of another compound after administration of the latter to a subject. Metabolites can be identified by techniques well-known in the art.

The invention also comprises kits, e.g., for the treatment, diagnosis, prophylaxis or prognosis of disease or injury. In one embodiment, the kit includes a composition of the invention containing an effective amount of a compound of the invention in unit dosage form. In some embodiments, the kit comprises an outer container or package. The kit can comprise a sterile container which contains a therapeutic; such sterile containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain kit embodiments, a composition of the invention is provided together with instructions for administering it to a subject. Instructions may include information about the use and effects of the composition. In one embodiment, the instructions will include at least one of the following: description of a composition of the invention, dosage schedule and administration protocols, precautions, warnings, indications, counter-indications, overdosage information, adverse reactions, animal pharmacology, clinical studies, and/or references. The instructions may be printed directly on a container (when present), or as a label applied to the container, or as a separate sheet, pamphlet, card, or folder supplied in, on or with the container. Thus, the instructions may be a separate item in the kit, or be imprinted embossed, molded or otherwise affixed to another item in the kit; instructions may be printed on an outer container and also included as an insert item in the kit.

Other features and advantages of the invention will be apparent from the detailed description, and from the claims.

DETAILED DESCRIPTION AND EXAMPLES

Definitions

Figure 1A:
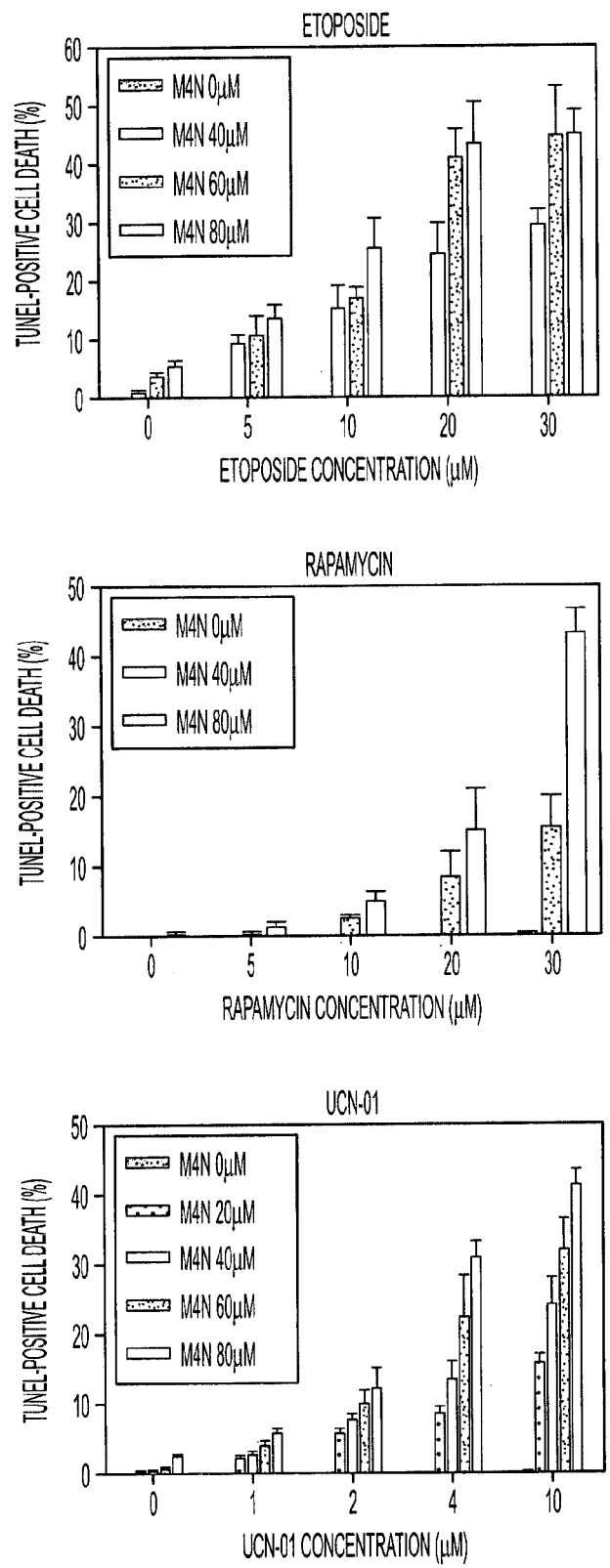
FIG. 1. Synergistic induction of TUNEL-positive cell death by the combination treatments of $M_4N$ with etoposide, rapamycin, or UCN-01 in LNCaP human prostate cancer cells. A: Synergistic induction of cell death by the combination treatments of $M_4N$ with etoposide, rapamycin, or UCN-01 in LNCaP cells. LNCaP cells were treated with $M_4N$ in the combination with etoposide, rapamycin or UCN-01 respectively at various concentrations of the drugs. The cell death was measured by the TUNEL assay at 24 hrs (etoposide, rapamycin) or 18 hrs (UCN-01) after the treatment. Data are presented as means (+/−) SD in triplicates. B: The Chou-Talalay plot for the combination treatments of $M_4N$ with etoposide, rapamycin, or UCN-01 in LNCaP cells. Combination index (CI)<1, +1, and >1 indicate synergism, additive effect, and antagonism. C: The cleavage of caspase-3-7 and −9, and ICAD in LNCaP cells treated by the combination treatments of $M_4N$ with etoposide, rapamycin, or UCN-01. The cleaved proteins were detected by the western blotting in LNCaP cells treated for 17 hrs. The concentration of $M_4N$, etoposide, rapamycin, and UCN-01 was 80 μM, 10 μM, 10 μM, and 2 μM respectively. β-Actin was used as a control. E: etoposide, Ra: rapamycin, U: UCN-01, M: $M_4N$. D: Caspase-7 enzymatic activity in LNCaP cells treated by the combination treatments of $M_4N$ with etoposide, rapamycin, or UCN-01. The caspase-7 enzymatic activity was detected in the cell extracts from LNCaP cells treated for 13 hrs. (−): control, E: etoposide, Ra: rapamycin, U: UCN-01. E: The effect of z-DEVD-fmk on the TUNEL-positive cell death induced by the combination treatment of $M_4N$ with etoposide, rapamycin, or UCN-01. The cell death was measured at 24 hrs after treatment. The concentration of z-DEVD-fmk, $M_4N$, etoposide, rapamycin, and UCN-01 was 50 μM, 80 μM, 10 μM, 20 μM, and 2 μM respectively. F: The effect of dominant negative PKCδ construct on the tunnel-positive cell death induced by the combination treatment of $M_4N$ with etoposide, rapamycin, or UCN-01. The cell death was measured at 24 hours after treatment the concentration of $M_4N$, etoposide, rapamycin, and UCN-01 was 80 μM, 20 μM, 20 μM, and 2 μM respectively.

By "agent" is meant a polypeptide, peptide, nucleic acid molecule, small molecule, or mimetic.

By "analog" is meant an agent having structural or functional homology to a reference agent.

By "cell substrate" is meant the cellular or acellular material (e.g., extracellular matrix, polypeptides, peptides, or other molecular components) that is in contact with the cell.

By "control" is meant a standard or reference condition.

By "disease" is meant any condition or disorder that damages or interferes with the normal function of a cell, tissue, organ or subject.

By "effective amount" is meant the amount of an agent required to ameliorate the symptoms of a disease relative to an untreated patient. The effective amount of an active therapeutic agent used to practice the present invention for the treatment of a disease or injury varies depending upon the manner of administration, the age, body weight, and general health of the subject. Ultimately, the attending clinician will decide the appropriate amount and dosage regimen.

By "fragment" is meant a portion of a polypeptide that has at least 50% of the biological activity of the polypeptide from which it is derived. This portion contains, preferably, at least 10%, 20%, 30%, 40%, 50%, 60%, 70%, 80%, or 90% of the entire length of the reference nucleic acid molecule or polypeptide. A fragment of a polypeptide or nucleic acid molecule may contain 10, 20, 30, 40, 50, 60, 70, 80, 90, or 100, 200, 300, 400, 500, 600, 700, 800, 900, or 1000 nucleotides or amino acids.

"HIF" refers to hypoxia inducible factor-1

"M$_4$N" refers to Tetra-O-methyl nordihyroguaiaretic acid, EM1421 or Terameprocol, each of which are synonyms.

"Lower alkyl" and "lower alkoxy" refer to alkyl and alkoxy groups of 1-6 carbon atoms.

By "modifies" is meant alters. In the context of the invention, an agent that modifies a cell, substrate, or cellular environment produces a biochemical alteration in a component (e.g., polypeptide, nucleotide, or molecular component) of the cell, substrate, or cellular environment.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, a "prodrug" is a pharmacologically inactive compound that is converted into a pharmacologically active agent by a metabolic transformation.

By "subject" is meant a mammal, including, but not limited to, a human or non-human mammal, such as a bovine, equine, canine, ovine, or feline.

By "therapeutic delivery device" is meant any device that provides for the release of a therapeutic agent. Exemplary therapeutic delivery devices include osmotic pumps, indwelling catheters, and sustained-release biomaterials.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "variant" is meant an agent having structural homology to a reference agent but varying from the reference in its biological activity. Variants provided by the invention include optimized amino acid and nucleic acid sequences that are selected using the methods described herein as having one or more desirable characteristics.

As used herein, "inhibiting" means slowing or stopping the growth of.

As used herein, "with" or "along with" means that the compounds are administered during the same course of treatment, but not necessarily simultaneously. Administration may occur seconds, minutes, or hours apart in time, but will preferably be closely spaced (at least minutes). The compounds should be administered for sufficient duration (e.g. daily) so that an effective dosage is achieved in plasma and in the target tumor cells.

Materials and Methods
Cell Culture

LNCaP human prostate cancer, DU145 human prostate cancer, PC3 human prostate cancer, MCF-7 human breast cancer, MDA-MB-231 human breast cancer, MDA-MB-468 human breast cancer, HT29 human colon cancer, K562 human myelogenous leukaemia, HepG2 human hepatoma, Hep3B human hepatoma, and LN229 human glioblastoma cancer cell lines were purchased from American Type Culture Collection (Manassas, Va.). OC24 human ascites ovarian cancer cell line was a generous gift from Dr. XXX (Johns Hopkins University, MD). LNCaP cell line was cultured in RPMI1640 medium supplemented with glucose (14 mM), pyruvate (1 mM), and fetal bovine serum (FBS) (10%). DU145 cell line was cultured in MEM supplemented with non-essential amino acids, glucose (21 mM), pyruvate (1 mM), and FBS (10%). PC3 cell line was cultured in F-12K medium supplemented with FBS (10%). MCF-7 cell line was cultured in DMEM supplemented with FBS (10%). OC24 cell line was cultured in RPMI1640 medium supplemented with FBS (10%) as suspension culture. MDA-MB-231 and 468 cell lines were cultured in Leibovitz's L15 medium supplemented with FBS (10%) under air. HT29 cell line was cultured in DMEM supplemented with glucose (25 mM) and FBS (10%). K562 cell line was cultured in RPMI1640 supplemented with FBS (10%). HepG2 and Hep3B cell lines were cultured in MEM supplemented with FBS (10%). LN229 cell line was cultured in DMEM supplemented with FBS (5%). All the tissue culture mediums contained penicillin (100 units/ml) and streptomycin (100 g/ml). Drugs were dissolved in dimethyl sulfoxide at the final concentrations in the medium less than 0.1%. When the cells were indicated to be cultured under hypoxic conditions, the cells were incubated at the oxygen concentration of 0.5% in the hypoxic chamber (BioSpherix Ltd, Lacona, N.Y.).

Reagents

Terameprocol ($M_4N$) (10 mg/ml in CPE 25/30 formulation) was supplied by Erimos Pharmaceutical, L.L.C. (Raleigh, N.C.), according to the method described (39). Etoposide, rapamycin, UCN-01, and Baflomycin $A_1$ were all from Sigma (Saint Louis, Mo.). Anti-hypoxia inhibitory factor (HIF)1α rabbit polyclonal antibody was from Novus Biologicals (Littleton, Colo.). Anti-BNIP3 mouse monoclonal antibody was from Abcam (Cambridge, Mass.). Anti-caspase-9 (full & cleaved), anti-cleaved caspase-3, anti-cleaved ICAD, anti-LC3B, anti-Beclin-1 polyclonal antibodies were all from Cell Signaling Technology. Both anti-caspase-7 (full & cleaved p34 fragment) and anti-caspase-7 antibody specific for p20 fragment rabbit polyclonal antibodies were from Cell Signaling Technology. Anti-BNIP3L polyclonal antibody was from Exalpha Biologicals (Watertown, Mass.). Anti-β-Actin monoclonal antibody was from Sigma (Saint Louis, Mo.). zDEVD-fmk was from Bachem Bioscience Inc. (King of Prussia, Pa.).

Computer Analysis about the Synergicity Between Drugs

The synergicity of combination drug treatments was analyzed by the Combosyn software (Combosyn Inc., Paramus, N.J.), according to the methodology by Chou & Talalay (40).

Drug Treatments for Animals

T-cell deficient male nude mice (nu/nu) were obtained from Charles River Laboratories (Wilmington, Mass.). Etoposide (4 mg/ml), rapamycin (3.75 mg/ml), UCN-01 (884 g/ml), and $M_4N$ (Terameprocol, 10 mg/ml) were formulated separately in CPE 25/30 vehicle (28) and used as single drugs. For drug combinations ($M_4N$/etoposide, $M_4N$/rapamycin, and $M_4N$/UCN-01), etoposide, rapamycin, or UCN-01 powder was further added to $M_4N$ in CPE 25/30 to make a final concentration of $M_4N$ (10 mg/ml) respectively with etoposide (4 mg/ml), rapamycin (3.75 mg/ml), or UCN-01 (884 g/ml) in CPE 25/30 formulation. These drugs were intravenously injected into the tail vein of mice at the daily dose of 0.1 ml per mouse. Therefore dosages of each injection were 1 mg/shot (for $M_4N$), 0.4 mg/shot (for etoposide), 0.375 mg/shot (for rapamycin), and 88.4 μg/shot (for UCN-01). The drug injections were performed once every day; beginning at day 3 until day 31 after tumor inoculation for the combination treatment with either etoposide or rapamycin and until day 25 after tumor inoculation for the combination treatment with UCN-01. After this the drugs were injected once a week for etoposide/rapamycin combination treatment and once every three days until day 35 for UCN-01 combination treatment. Protocols used in this study were approved by the Institutional Animal Care and Use Committee at the Johns Hopkins University, Department of Biology.

Surgical Orthotopic Implantation of LNCaP Tumors

LNCaP cells growing subconfluently were collected into the tissue culture medium without fetal bovine serum and antibiotics. The cell concentration was adjusted by the same medium. After fifty μl of the medium containing certain number of cancer cells (about $2 \times 10^6$ cells) had been mixed together with the same volume of Matrigel (BD science, Bedford, Mass.), the combined solution was injected into the skin of nude mice. The tumor tissue growing subcutaneously was used for surgical orthotopic implantation. The operation was performed according to the method described by Wang et al. (41). The tumor tissue extracted from the skin was excised into pieces of about 2 mm diameter. After nude mice were anesthetized by 2,2,2-Tribromoethanol (Aldrich Chemical Co. Inc., Milwaukee, Wis.), a small incision was made at the abdomen of each mouse and a tumor tissue piece was implanted in the neighbor of the prostate of each mouse. Eight days after the operation, the injection of drugs was started. The drugs were injected intravenously every day. The size of subcutaneous tumors was estimated according to Bissery et al. (42).

Implantation of OC24 Ovarian Cancer Cells

OC24 cells growing subconfluently were collected into the tissue culture medium without fetal bovine serum and antibiotics. The cell concentration was adjusted by the same medium. The cell solution containing $5 \times 10^4$ cells was injected into the peritoneal cavity of each nude mouse at the day 0. The drug treatment started from day 3. For the estimation of the effect of the drug treatment, the volume of ascites fluids and of abdominal tumors was measured.

Apoptosis Assay

Simple TUNEL assay was conducted by using TUNEL apoptosis detection kit (Upstate, Temecula, Calif.) with some modification. The cells were cultured in 12-well microwell culture dishes (Corning Inc., Corning, N.Y.). After the treatment, both the cells floating in the tissue culture medium and the cells attached to the bottom of microwell dishes were collected together into plastic tubes. After the cells were spun down, they were fixed with 10% formaldehyde in PBS (−) for 5 minutes and stored in PBS (−). The fixed cell samples were put on glass slides and dried in the air. The glass slides with the fixed cells were first incubated in the solution containing 0.05% Tween-20, 0.2% BSA in PBS (−) for 15 minutes at room temperature. The samples were then treated with terminal deoxytransferase and biotin-dUTP included in the TUNEL assay kit for 60 minutes at room temperature, according to the company's protocol. After the incubation, the samples were incubated with avidin-biotin complex (ABC reagent, Vector Laboratory Inc.) for 30 minutes at room temperature. After the extensive washing with PBS (−), the DNA terminal endings of the samples were exposed by the peroxidase reaction using DAB as a substrate (Peroxidase substrate kit (DAB), Vector Laboratory Inc., Burlington, Calif.). The samples were counterstained by methyl green and embedded in VectaMount (Vector Laboratory Inc.).

Enzymatic Assay for caspase-7

The enzymatic assay specific for caspase-7 was performed using a CaspSELECT caspase-7 immunoassay kit (BioVision, Mountain View, Calif.). This assay is based on the calorimetric assay with DEVD-afc. Since DEVD-afc can be a substrate for either caspase-3 or 7, only caspase-7 is selected from cell extracts by anti-caspase-7 antibody which is coated on microtiter plates. Briefly the microtiter plates were coated with anti-caspase-7 antibody overnight at 4 C and blocked with a blocking solution for 30 minutes at room temperature. The cell extracts were applied to the microtiter plates. After washing the microtiter plates, the substrate DEVE-afc was added to the plates and incubated for about three hours. The fluorescence was measured by a microtiter plate fluorescence reader Infinite 200 (Tecan, Switzerland).

Immunocytochemistry

Cells were cultured on glass cover slips coated with poly-L-ornithine (Sigma, Saint Louis, Mo.). At 5 hrs after treatment with drugs, the cells were fixed with 10% formaldehyde in diluted in PBS (−) and washed with PBS (−) three times. After permeabilized by 0.2% Tryton X-100 and 1% goat serum diluted in PBS (−), the cells were blocked by PBS (−) containing 5% goat serum. The cells were then incubated with primary antibodies diluted in PBS (−) containing 0.5% bovine serum albumin (BSA), and with secondary antibodies, which is anti-IgG conjugated with fluorescein (Vector Laboratories, Burlingame, Calif.), diluted in PBS (−) containing 0.5% BSA. The samples were embedded in Vectashield mounting medium (Vector Laboratories, Burlingame, Calif.) containing DAPI for nuclear counterstaining. The cells were observed through B29/Zeiss LSM 510 µMETA (with 405 nm laser) laser confocal microscope (Carl Zeiss, Germany).

Histology

The lungs were excised from the tumor-bearing mice and fixed in 10% formalin diluted in PBS (−). The tissues were sectioned and stained with hematoxylin and eosin under the standard methodology by Paragon (Baltimore, Md.). The specimens were observed through Zeiss Axioplan microscope with 2.5× plan neoflour objective (Carl Zeiss, Germany). The data acquisition was done with Slidebook 4.2 software.

Western Blotting

After cells had been grown in 25 mm$^2$ flasks and treated with reagents, the cells were washed with PBS (−) three times and suspended in RIPA buffer (150 mM NaCl, 50 mM Tris-HCl (pH 8.0), 0.1% SDS, 1% NP40, and 0.5% deoxycholate) supplemented with protease inhibitor cocktail (Calbiochem, San Diego, Calif.). The sample volumes were adjusted by the total protein amount. Protein assay was performed by Bio-Rad Protein Assay (Bio-Rad Laboratories, Inc. Hercules, Calif.). The samples were resolved by the standard SDS-polyacrylamide gel electrophoresis and transferred to nitrocellulose membrane (Amersham Biosciences, Bjorkgatan, Sweden). The membranes were blocked with skim milk, and incubated with primary antibodies at 4° C. overnight and then with secondary antibody conjugated with horse radish peroxidase at room temperature for 2 hrs. The signals were detected by western blot chemiluminescence reagent plus (New England Nuclear Life Science Products, Boston, Mass.).

Northern Blotting

RNA was extracted from the cells by a Trizol Reagent (Invitrogen, Carlsbad, Calif.). Twentyfive µg of RNA per lane was dissolved on the 1.5% agarose gel containing 20 mM NaPO$_4$ (pH 6.8) and 6% formaldehyde. RNA was transferred to a Nytran SPC membrane (Sigma-Aldrich, St. Louis, Mo.). The probe for BNIP3 was derived from a 199 bp fragment DNA generated by RT-PCR using a SuperScript III First-Strand Synthesis System for RT-PCR (Invitrogen, Carlsbad, Calif.), 5'-primer 'gctcctgggtgaactgcac' and 3'-primer 'gtttcagaagccctgttggt'. The PCR fragment was cloned into a topo vector (Invitrogen, Carlsbad, Calif.). After midi-prep, the DNA fragment was excised from the vector and dissolved on the 2% agarose gel and purified. The extracted DNA fragment was labeled by $^{32}$P-αdATP, Klenow fragment, and random hexagonal primers. After unincorporated $^{32}$P-αdATP was removed by a Sephadex G-50 spun column, the labeled DNA fragment was used as a probe. After hybridization, the membrane was washed and autoradiographed to a BioMax MR film (Kodak, Rochester, N.Y.).

The Measurement of Mitochondrial Membrane Potential ($\Delta\Psi_m$)

The cells were cultured in 6 well microwell dishes and treated with the culture medium containing JC-1 dye (Cayman Chemical, Ann Arbor, Mich.) for 30 min, according to the company's protocol. After the cells had been washed carefully, they were treated with M4N for 5 hrs. The cells were observed through B29/Zeiss LSM 510 µMETA laser confocal microscope (Carl Zeiss, Germany). The cell images were captured by two different excitation lights (with 488 nm argon-ion and 568 nm argon-krypton lasers). Both JC-1 monomer and J-aggregates are detected by 488 nm excitation light while only J-aggregates are detected by 568 nm excitation light. The ratio of the intensity of the emission light excited by 568 nm light to that of the emission light excited by 488 nm light at every pixel of images (The ratio should indicate the mitochondrial potential) was calculated by the imaging software (Carl Zeiss, Germany). In the figure the ratio was shown by pseudo color. Red color indicates high ratio (high potential) while dark blue indicates low ratio (low potential). Yellow through green to light blue represents medium ratio (medium potential).

Example 1

Figure 1B:
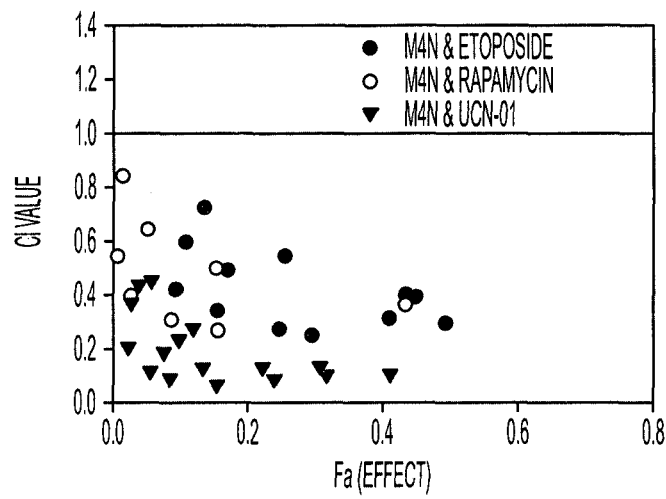
Figure 1C:
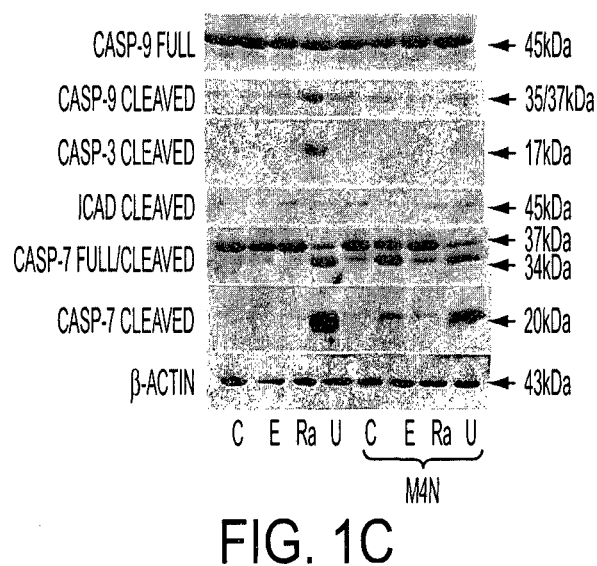
Figure 1D:
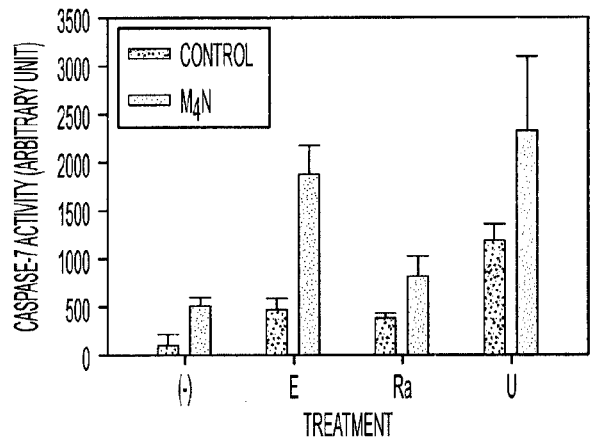
Figure 1E:
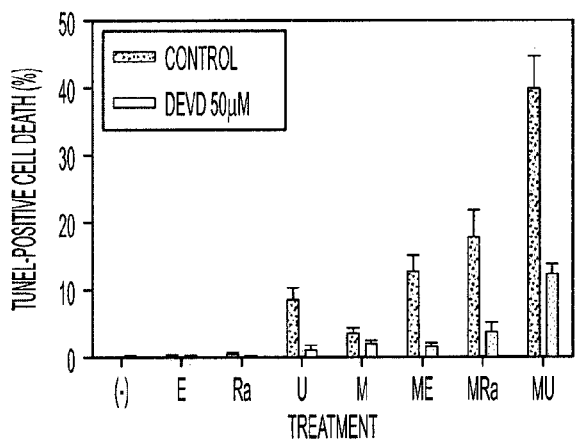
Figure 1F:
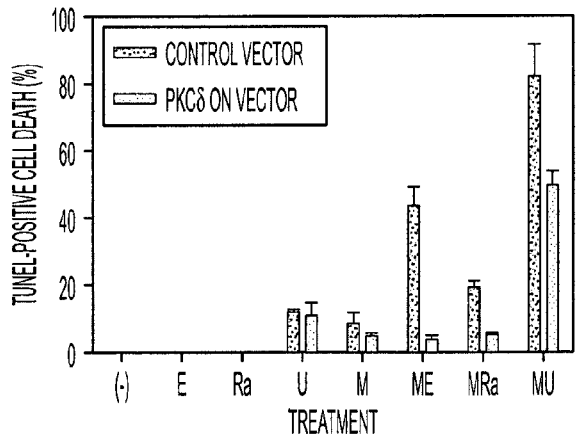

Synergistic Induction of Cell Death by the Combination Treatment of M$_4$N with Etoposide, Rapamycin, and UCN-01 in LNCaP Human Prostate Cancer Cells The efficacy of the combination treatment of M4N with three anticancer drugs, etoposide, rapamycin, and UCN-01 to induce cell death was examined for LNCaP human prostate cancer cells with TUNEL assay. We chose these anticancer drugs trying to diversify the mechanisms in which the anticancer drugs work (43-45). M4N was shown to induce TUNEL-positive cell death synergistically with all these anticancer drugs (FIG. 1A). Chou-Talalay's plot (40) confirmed that the combination treatments worked synergistically for all three drugs at all the concentrations of the drugs at which the effect of the drugs was examined (FIG. 1B). The CI values indicated that the M$_4$N/etoposide and M$_4$N/rapamycin combination treatments were strongly synergistic while the M$_4$N/UCN-01 combination treatment was very strongly synergistic (FIG. 1B). To see the involvement of caspases for the cell death induced by the combination treatment, the expression of the cleaved products (which are active forms) of caspase-3, 7, and 9, and ICAD was examined (FIG. 1C). A great expression of cleaved caspase-3 and 9 was detected only in the cells treated with UCN-01 alone. M$_4$N, etoposide, and rapamycin didn't induce the cleavage in caspase-3 and 9. To our surprise, the combination treatment of M$_4$N with UCN-01 didn't induce caspase-3 and 9 cleavages either, which indicates that M$_4$N interferes in the ability of UCN-01 to induce activation of caspase-3 and 9. On the contrary, the cleavage products of caspase-7 (20 and 34 kDa) were detected in the cells treated under many different conditions (FIG. 1C). UCN-01 treatment alone induced caspase-7 cleavage to a great amount. Unlike caspase-3 and 9, M$_4$N didn't interfere in the ability for UCN-01 to induce caspase-7 cleavage. Furthermore, the combination treatment of M$_4$N and etoposide induced much more caspase-7 cleavage than either M$_4$N treatment alone or etoposide treatment alone. M$_4$N treatment alone and the combination treatment of M$_4$N with rapamycin induced a small amount of caspase-7 cleavage while rapamycin treatment alone failed to induce caspase-7 cleavage at all. ICAD cleavage products were not detected under any conditions. To confirm caspase-7 activation detected by the western blotting, the calorimetric assay for active caspase-7 was performed (FIG. 1D). The calorimetric assay data overall confirmed the western blotting data (FIG. 1C). Briefly M$_4$N treatment alone, etoposide treatment alone, or rapamycin treatment alone induced only a small amount of caspase-7 activation. UCN-01 treatment alone induced caspase-7 activation to some extent. The combination treatment of M$_4$N with etoposide, rapamycin, or UCN-01 induced much more caspase-7 activity than the treatment of etoposide, rapamycin, or UCN-01 alone respectively. Additionally the effect of caspase-3 and 7 inhibitor, zDEVD-fmk on the cell death induced by the combination treatment was examined (FIG. 1E). Since caspase-3 cleaved product was observed only in the cells treated with UCN-01 (FIG. 1C), zDEVD-fmk, an inhibitor specific for caspase-3 and 7, is considered mainly to inhibit caspase-7 activation in the cells treated otherwise. The TUNEL assay data shows that zDEVD-fmk inhibited a large portion of the cell death induced by the combination treatments (FIG. 1E), which indicates that caspase-7 is involved in this type of cell death. The fact that zDEVD-fmk couldn't inhibit all the cell death suggests that there are other cell death machineries involved in the cell death than caspase-7-related mechanism.

Example 2

Analysis for Autophagy in the Cells Treated with the Combination Treatment of M$_4$N with Etoposide, Rapamycin, and UCN-01

Figure 2A:
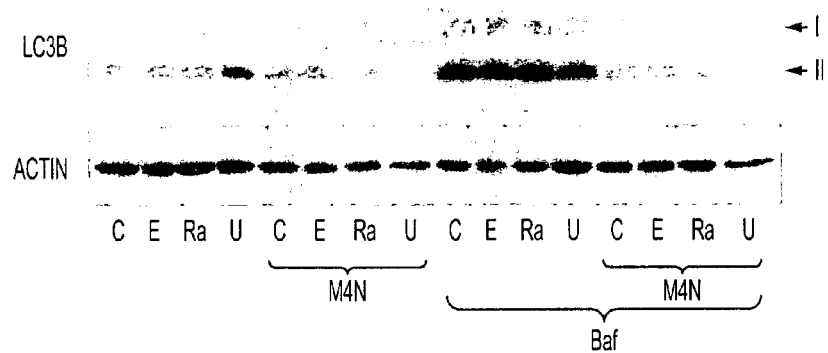
FIG. 2. A: The expression of LC3B in LNCaP cells treated with the combination drug of M4N with etoposide, rapamycin, or UCN-01, detected by the western blotting. The LC3B-I&II expression was examined by the western blotting in LNCaP cells treated with the combination treatment of $M_4N$ with three different drugs (etoposide, rapamycin, and UCN-01) for 18 hrs in the either presence or absence of Baflomycin $A_1$ (100 nM), an autophagosome degradation inhibitor. The concentration of $M_4N$, etoposide, rapamycin, and UCN-01 was 80 μM, 10 μM, 10 μM, and 2 μM respectively. β-Actin was used as a control. C: Control, E: etoposide, Rap: rapamycin, U: UCN-01, Baf: Baflomycin $A_1$. B: The expression of LC3B in LNCaP cells treated with the combination drug of $M_4N$ with etoposide, rapamycin, or UCN-01, detected by the confocal microscopy. The LC3B expression was examined by the confocal microscopy for LNCaP cells treated with the combination treatment of $M_4N$ with three different drugs (etoposide, rapamycin, and UCN-01) for 6 hrs in the presence of Baflomycin $A_1$ (100 nM), an autophagosome degradation inhibitor, and stained with anti-LC3B antibody by immunocytochemical methodology. LC3B staining was done by FITC staining (green). The concentration of $M_4N$, etoposide, rapamycin, and UCN-01 was 80 μM, 10 μM, 10 μM, and 2 μM respectively. For the control image, see FIG. 4A. Eto: etoposide, Rap: rapamycin, U: UCN-01, M: $M_4N$, Baf: Baflomycin $A_1$.
Figure 2B:
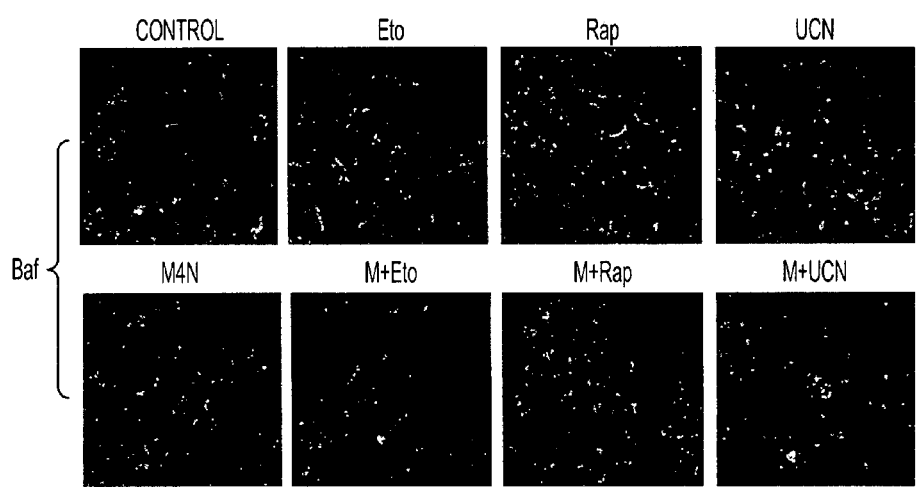
Figure 3A:
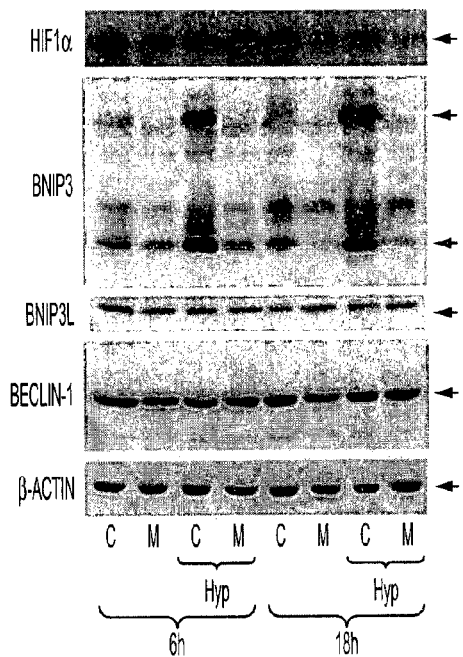
FIG. 3. A: The effect of $M_4N$ and hypoxia on the expression of HIF1α, BNIP3, BNIP3L, and Beclin-1. The expression of HIF1α, BNIP3, BNIP3L, and Beclin-1 was examined by the western blotting in LNCaP cells treated with $M_4N$ under either normoxic or hypoxic condition for either 6 or 18 hr. The concentration of $M_4N$ was 80 μM. β-Actin was used as a control. C: Control, M: $M_4N$, Hyp: hypoxic condition. B: The effect of $M_4N$ and hypoxia on the mRNA expression of BNIP3 gene at 2 and 6 hrs after treatment. The mRNA expression of BNIP3 gene was examined by the Northern blotting in LNCaP cells treated with $M_4N$ under either normoxic or hypoxic condition for either 2 or 6 hr. The concentration of $M_4N$ was 80 μM. β-Actin was used as a control. C: Control, M: $M_4N$, Hyp: hypoxic condition. C: The effect of M4N on the mitochondrial membrane potential ($\Delta\Psi_m$). The $\Delta\Psi_m$ was measured at 5 hrs after treatment with M4N (80 μM) using JC-1 dye. The ratio of the intensity of the emission light excited by 568 nm light to that of the emission light excited by 488 nm light at every pixel of images (The ratio should indicate the mitochondrial potential) was calculated by the imaging software (Carl Zeiss, Thornwood, N.Y.). In the figure the ratio was shown by pseudo color. Red color indicates high ratio (high potential) while dark blue indicates low ratio (low potential). Yellow through green to light blue represents medium ratio (medium potential).

It has been elucidated that autophagy as well as apoptosis/necrosis plays a very important role in anticancer activity of chemotherapeutic drug treatments. Then next the status of autophagy in the cells treated with the combination treatments of M$_4$N with etoposide, rapamycin or UCN-01 was examined. LC3B-II expression is known to be in a good correlation with autophagy activity of the cells (46). The left half of FIG. 2A shows that the LC3B-II expression (without Baflomycin A$_1$ treatment), which reflects the concurrent activity of autophagy, was not much modulated by any of the combination treatments at 18 hrs after treatment. However this data merely shows the autophagic activity at the time point of 18 hrs after treatment since LC3B-II is both synthesized and disintegrated very fast during the process of autophagy. To measure the net activity of autophagy after the treatment with the drugs, Baflomycin A$_1$, an inhibitor for autophagosome degradation, was added to the experimental system to prevent the degradation of LC3B-II. Since the degradation of LC3B-II stops in the presence of Baflomycin A$_1$, the net flow of LC3B-II formation which indicates the net activity of autophagy from the period starting at the drug treatment and ending at the sample collection will be assessed. The right half of FIG. 3A shows that the net LC3B-II formation (in other words, the net autophagic activity) was almost totally suppressed by M$_4$N. FIG. 2B shows the images of autophagosomes which are revealed by the immunological staining for LC3B in the cells treated with the combination treatments in the presence of Baflomycin A$_1$. The immunological staining clearly shows that M$_4$N treatment reduced the net amount of autophagosomes formed during the period starting at the drug treatment and ending at the sample collection (6 hrs after treatment) very dramatically both in the control cells and in the cells treated with any one of the combination treatments. All the data in FIG. 2 overall indicate that M$_4$N has a very strong activity to block autophagy.
Inhibitory Effect of M$_4$N on BNIP-3 Expression and Mitochondrial Membrane Potential Depolarization ($\Delta\Psi_m$)

Figure 3B:
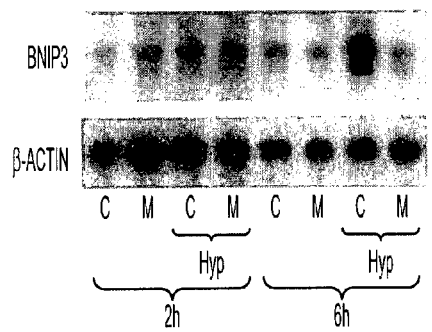

BNIP3 is a member of Bcl-2 family proteins which sends pro-apoptotic signal to mitochondria and induces mitochondrial membrane potential depolarization. A recent report indicated that BNIP3 plays an important role in the mechanism of the autophagy induction by hypoxic stress which confers the cells the ability to resist hypoxic injuries. This implies that BNIP3 is involved in autophagy as well as cell death. To see a possible role of BNIP3 in the synergistic induction of cell death by the combination treatments of M$_4$N with other anticancer drugs and the inhibitory effect of M$_4$N on autophagy, the protein expression (FIG. 3A) and mRNA expression (FIG. 3B) of BNIP3 were examined. Since BNIP3 is known to be activated more under hypoxic conditions (24), BNIP3 expression was examined in both normoxic and hypoxic conditions (FIGS. 3A&B). The western blotting data shows that M$_4$N blocks BNIP3 protein expression under either normoxic or hypoxic condition (FIG. 3A). Previously it was shown that BNIP3 expression is augmented by hypoxia through both hypoxia inhibitory factor (HIF)1α-dependent and nondependent pathways (24). In this study HIF1α expression was augmented by the 6 hr exposure of the cells to hypoxia (FIG. 3A). $M_4N$ did not have much effect on HIF1α expression at this time point although BNIP3 expression was already significantly reduced by $M_4N$ treatment, which indicates that the reduction of BNIP3 expression by $M_4N$ was not caused by the indirect effect of $M_4N$ on HIF1α and then BNIP3, but that it was probably caused by the direct effect of $M_4N$ on BNIP3 gene itself. In fact the Northern blotting data clearly showed that $M_4N$ suppressed the increase of BNIP3 mRNA expression facilitated by 6 hr exposure to hypoxic condition (FIG. 3B). Interestingly $M_4N$ reduced HIF1α expression induced by the 18 hr exposure of the cells to hypoxia. Beclin-1 expression was not affected by any procedure (FIG. 3A), which is consistent with the findings by other laboratory indicating that the constitutive expression of Beclin-1 is important in autophagy (24). The expression of BNIP3L, a homologue of BNIP3, was only slightly reduced by $M_4N$ treatment (FIG. 3A), indicating that $M_4N$ specifically modulated BNIP3 expression.

Figure 3C:
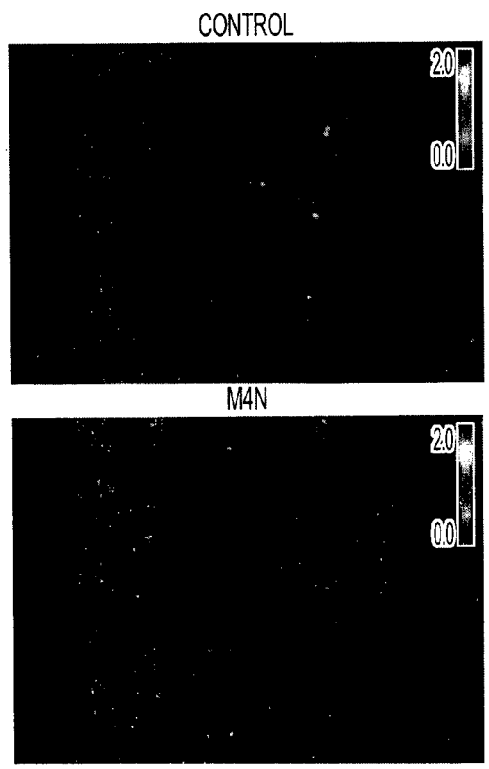

Since BNIP3 functions to activate mitochondria-related cell death machinery and induce mitochondrial membrane depolarization, the effect of $M_4N$ on the mitochondrial membrane potential ($\Delta\Psi_m$) was examined (FIG. 3C). The fluorescence image data using JC-1 dye shows that $M_4N$ treatment hyperpolarized mitochondria membrane potential, which is consistent with the assumption that the reduction of BNIP3 expression by $M_4N$ treatment blocks the mitochondrial membrane depolarization signals derived from BNIP3. The data is also consistent with the $M_4N$-mediated blockage of caspase-9 and 3 activation induced by UCN-01 treatment (FIG. 1C), since the activation of caspase-9 and then caspase-3 is well established as the direct consequence of activation of mitochondria-related cell death machinery (15).

Example 3

Figure 4A:
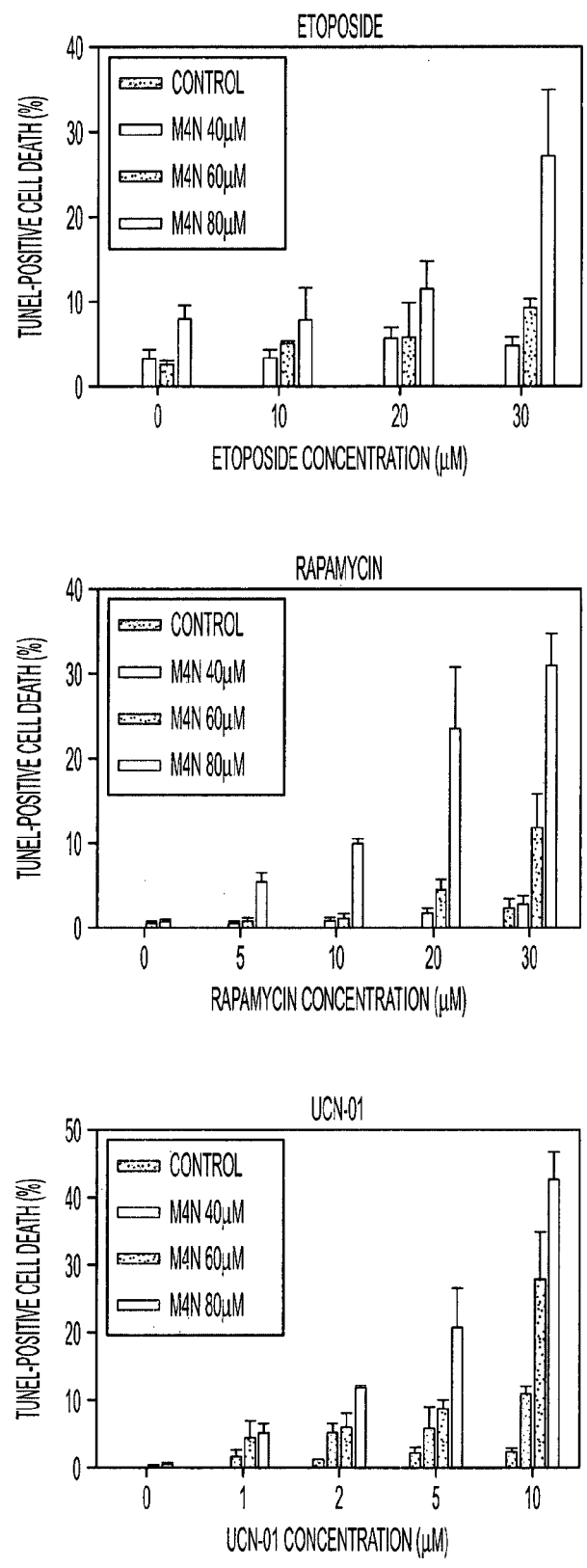
FIG. 4. Effect of the combination treatments of $M_4N$ with etoposide, rapamycin, or UCN-01 on cell death and autophagy in MCF-7 human breast and HepG2 human hepatic cancer cells. A: Synergistic induction of cell death by the combination treatments of $M_4N$ with etoposide, rapamycin, or UCN-01 in MCF-7 cells. MCF-7 cells were treated with $M_4N$ in the combination with etoposide, rapamycin or UCN-01 respectively at various concentrations of the drugs. The cell death was measured by the TUNEL assay at 23 hrs (rapamycin, UCN-01) or 32 hrs (etoposide) after the treatment. Data are presented as means (+/−) SD in triplicates. B: The Chou-Talalay plot for the combination treatments of $M_4N$ with etoposide, rapamycin, or UCN-01 in MCF-7 cells. Combination index (CI)<1, +1, and >1 indicate synergism, additive effect, and antagonism. C: Synergistic induction of cell death by the combination treatments of $M_4N$ with etoposide, rapamycin or UCN-01 in HepG2 cells. HepG2 cells were treated with $M_4N$ (80 μM) in combination with etoposide (20 μM), rapamycin (20 mM0 or UCN-01 (5 μM) respectively at various concentration s of the drugs. Cell death was measured by the tunnel assay 24 hours after treatment. Data are presented as means (+/−) SD in triplicate. D: The expression of LC3B in MCF-7 and HepG2 cells treated with the combination drug of M4N with etoposide, rapamycin, or UCN-01, detected by western blotting. The LC3B-I&II expression was examined by the western blotting in MCF-7 and HepG2 cells treated with the combination treatment of $M_4N$ with three different drugs (etoposide, rapamycin, and UCN-01) for 15 hrs in either the presence or absence of Bafilomycin A$_1$ (100 nM), an autophagosome degradation inhibitor. The concentration of M$_4$N, etoposide, rapamycin, and UCN-01 was 80 μM, 20 μM, 20 μM, and 5 μM respectively. β-Actin was used as a control. C: Control, E: etoposide, Rap: rapamycin, U: UCN-01, Baf: Bafilomycin A$_1$. E: The cleavage of caspase-3-7 and -9 in MCF-7 and HepG2 cells treated by the combination treatments of M$_4$N with etoposide, rapamycin, or UCN-01. The cleaved proteins were detected by the western blotting in MCF-7 and HepG2 cells treated for 17 hrs. The concentration of M$_4$N, etoposide, rapamycin, and UCN-01 was 80 μM, 20 μM, 20 μM, and 5 μM respectively. β-Actin was used as a control. E: etoposide, Ra: rapamycin, U: UCN-01, M: M$_4$N.
Figure 4B:
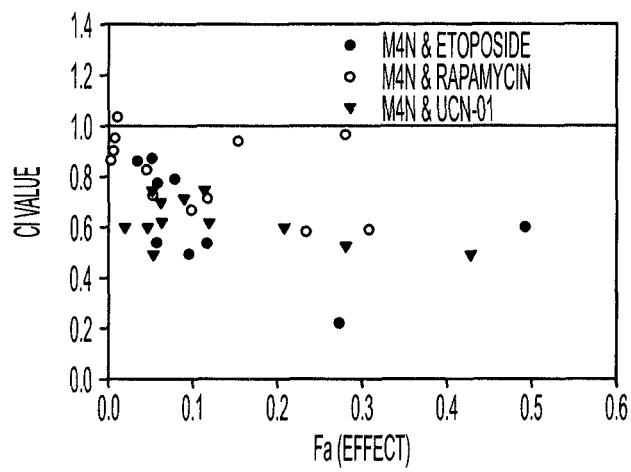
Figure 4C:
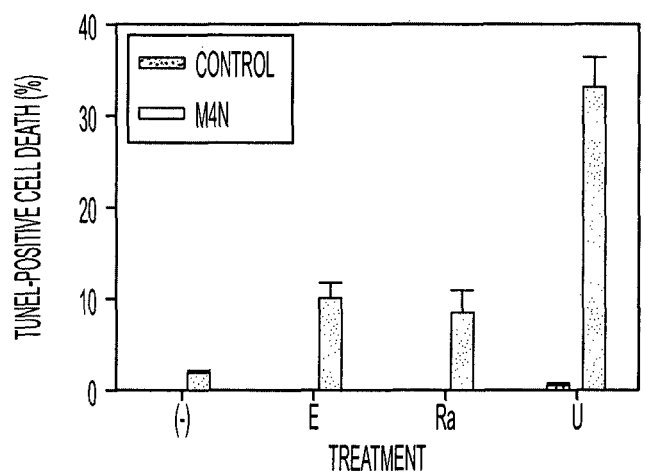

Effect of the Combination Treatments of $M_4N$ with Etoposide, Rapamycin, and UCN-01 on Cell Death and Autophagy in Human MCF-7 Breast and HepG2 Hepatic Cancer Cells The effect of the combination treatments on cell death and autophagy was examined in two cell lines other than LNCaP cells. FIGS. 4A and B shows that a synergistic induction of cell death was detected in MCF-7 human breast cancer cells as well as LNCaP cells. Caspase-3 and 9 cleavage products were not detected in MCF-7 cells treated with any combination drugs examined here, which indicates that the mitochondria-related cell death pathway is not functional in this cell line (FIG. 4C) although a substantial amount of cell death was detected by the combination drug treatments in this cell line as much as in LNCaP cells (FIG. 4A). On the contrary caspase-7 cleavage was detected in MCF-7 cells treated with UCN-01 treatment alone, the combination treatments of $M_4N$ with either etoposide or UCN-01 (FIG. 4C). Similarly any treatments induced a substantial amount of neither caspase-3 or 9 cleavage in HepG2 human hepatic cancer cells (FIG. 4C), which indicates that mitochondrial cell death pathway is broken in both MCF-7 and HepG2 cells as seen in many cancer cells. Interestingly a small amount of caspase-3 cleaved product was detected in HepG2 cells treated with UCN-01 alone while there was no caspase-3 cleavage detected in the cells treated with the combination treatment of $M_4N$ with UCN-01 (FIG. 4C). This is reminiscent of the caspase-3 cleavage in LNCaP cells treated with either UCN-01 alone or the combination treatment of $M_4N$ with UCN-01 (FIG. 1C). On the contrary a great deal of caspase-7 cleavage product was detected in HepG2 cells treated with UCN-01 or the combination treatment of $M_4N$ with UCN-01 while a small amount of caspase-7 cleavage product was detected in the cells treated with etoposide or rapamycin regardless of a concomitant treatment with $M_4N$ (FIG. 4C). Overall the TUNEL assay data indicates that the combination treatment is able synergistically to induce cell death in the cancer cells whose mitochondrial cell death machinery is broken, such as MCF-7 cells (FIGS. 4A & B). Meanwhile the western blotting data shows that caspase-7 cleavage is either enhanced or unchanged in the cells treated with the combination treatments in these cell lines as well as in LNCaP cells (FIG. 4C).

Figure 4D:
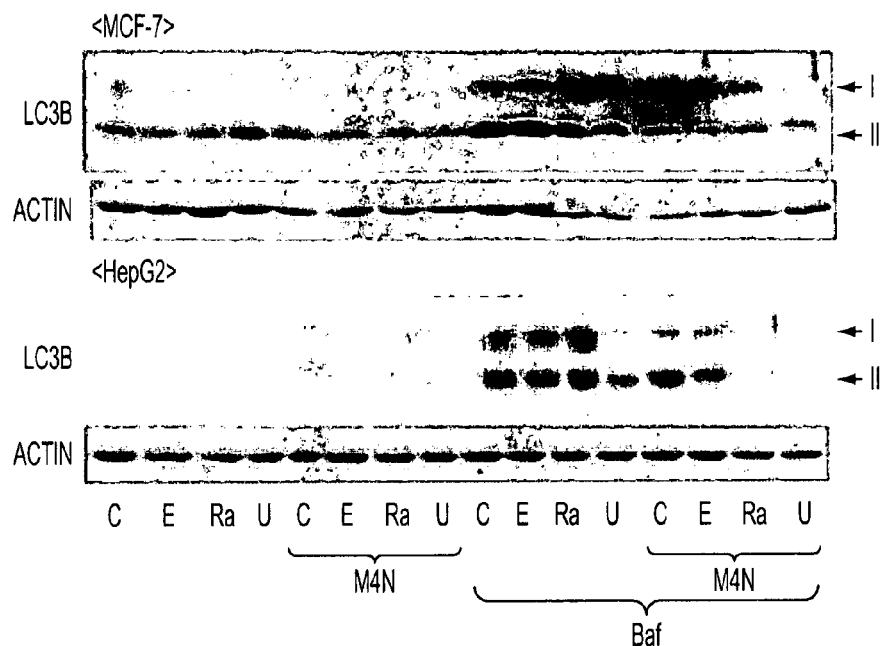
Figure 4E:
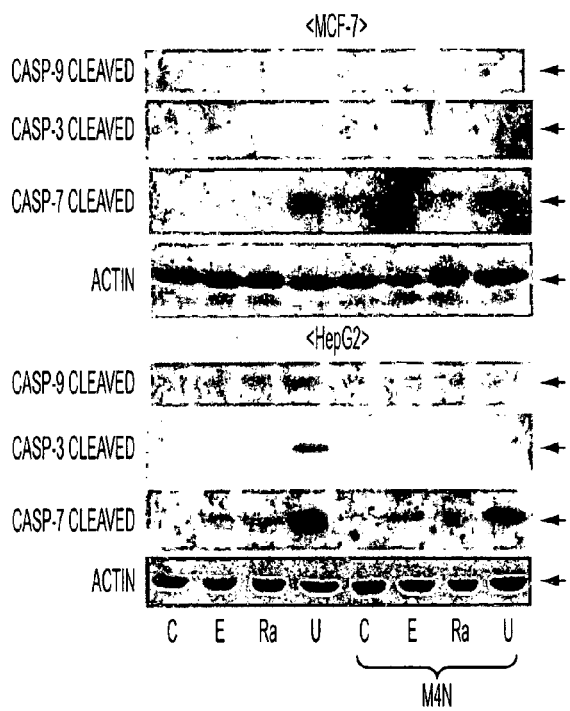

The effect of $M_4N$ on autophagy was examined using the western blotting for LC3B-II in the presence of Baflomycin $A_1$ in MCF-7 and HepG2 cells (FIG. 4D). The western blotting data shows that $M_4N$ blocks autophagy in these cell lines as well as in LNCaP cells, indicating that the suppressive effect of $M_4N$ on autophagy is ubiquitous among cancer cells to some degrees.

Effect of the Combination Treatments of $M_4N$ with Etoposide and Rapamycin on the Life-Span and Lung Metastasis in Nude (nu/nu) Mice Orthotopically Implanted with LNCaP Tumors.

Figure 5A:
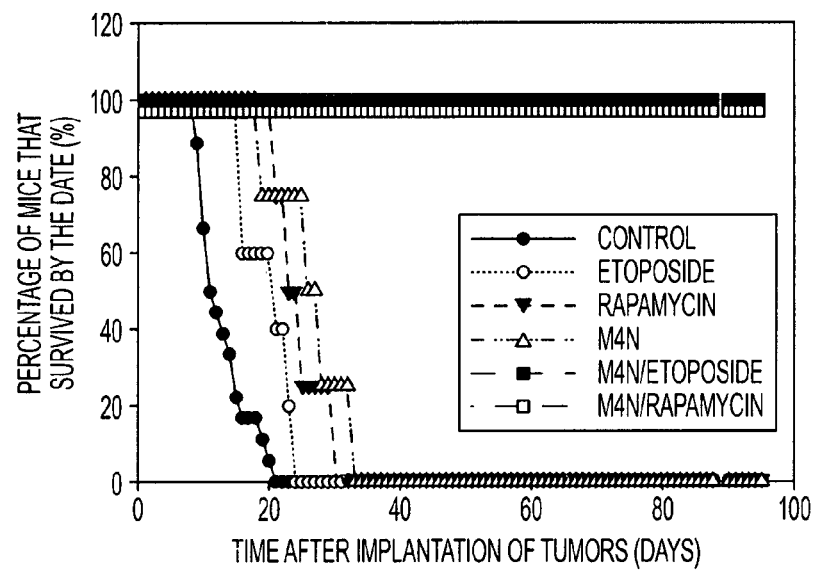
FIG. 5. Effect of combination treatment of M$_4$N with either etoposide or rapamycin on nude (nu/nu) mice orthotropically implanted with LNCaP tumors. LNCaP tumors were orthotropically implanted into the vicinity of prostate glands in male nude mice. A: Effect of the combination treatment of M$_4$N with either etoposide or rapamycin on the life-span of tumor-bearing mice. The percentage of mice that have died by the date after tumor inoculation was shown for each group. The numbers of mice in each group were 18, 5, 4, 4, 9 and 5 for the control, etoposide alone, rapamycin alone, M$_4$N alone, M$_4$N & etoposide, and M$_4$N & rapamycin group respectively. Dosages of each injection were 1 mg/shot (for M$_4$N), 0.4 mg/shot (for etoposide), and 0.375 mg/shot (for rapamycin). Drug injections started 3 days after implantation of tumors. Drugs were administered 7 days a week for four weeks. After that drugs were injected once a week. B: Histological images of the lung from the tumor-bearing mice treated with different methods. The lung sections were stained with hematoxylin and eosin and observed under the 100×-magnification. M indicates metastasis lesions. Cont, Eto, Rap, M$_4$N, M$_4$N+Ly, M$_4$N+Ro+Ly, M$_4$N+Eto, and M$_4$N+Rap indicate 'control', 'Etoposide alone', 'Rapamycin alone', 'M$_4$N alone', 'M$_4$N and Ly294002 combination', 'M$_4$N, Rottlerin, and Ly294002 combination', 'M$_4$N and Etoposide combination', and 'M$_4$N and Rapamycin combination'.
Figure 5B:
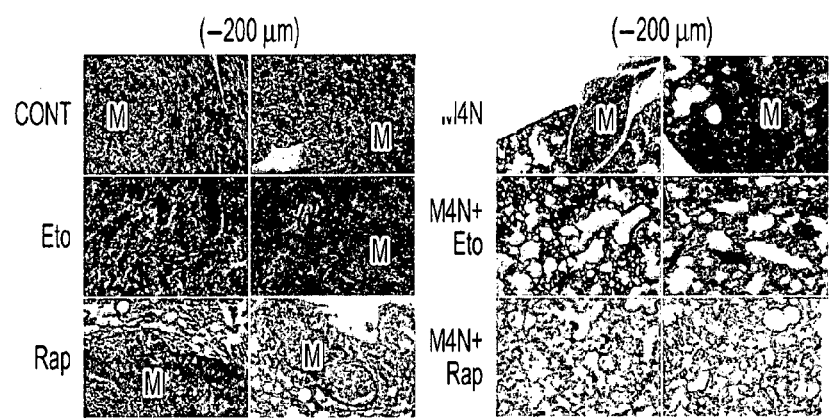

The tissue culture data with LNCaP cells (FIGS. 1A & B) showing the synergistic induction of cell death by the combination treatment of either $M_4N$/etoposide or $M_4N$/rapamycin prompted us to examine the anticancer efficacy of this combination drug regimen in xenograft animal experiment. We administered the compounds to mice intravenously using CPE (25/30) solvent system (39). The data for survival rate after tumor inoculation (FIG. 5A) shows that all the LNCaP tumor-bearing mice treated with $M_4N$ and either etoposide (9 out of 9 mice) or rapamycin (5 out of 5 mice) survived beyond 100 days after the implantation while all the mice treated with a single drug (etoposide, rapamycin, or $M_4N$) did not survive beyond 34 days after the implantation (all the control mice died before 20 days after the implantation). Histological data (FIG. 5B) shows that the lungs from all the mice treated with $M_4N$ with either etoposide or rapamycin did not develop any obvious lung metastasis (etoposide: 0 out of 5 mice, rapamycin: 0 out of 3 mice) while many of the lungs from the mice treated with a single drug (etoposide, rapamycin, or $M_4N$) develop obvious lung metastasis (etoposide: 3 out of 5 mice, rapamycin: 3 out of 4 mice, $M_4N$: 2 out of 4 mice).

Example 4

Cell Death Induced by the Combination Treatment of $M_4N$ with UCN-01 in Various Tissue Culture Cells So far we have examined the synergistic induction of cell death based on $M_4N$ with other anticancer drugs mainly using LNCaP human prostate cancer cell line in this study other than the data with MCF-7 and HepG2 cells in FIG. 4. All these data shows that the combination treatment of $M_4N$ with UCN-01 induced more cell death in all cell lines used so far, which prompted us to examine further the efficacy of the combination drug treatment of $M_4N$ with UCN-01. First of all we examined the cell death in various cell lines treated with the combination treatment of $M_4N$ with UCN-01. The TUNEL assay data (FIG. 6) shows that $M_4N$ synergistically induce cell death with UCN-01 in the nine out of twelve cancer cell lines that we examined, which included LN229 glioblastoma cells, HT29 colon cancer cells, three different prostate cancer cells (LNCaP, DU145, and PC3), three different breast cancer cells (MCF-7, MDA-MB231, and MDA-MB468), and HepG2 hepatic cancer cells. In the remaining three cell lines (K562 leukemia cells, OC24 ovarian cancer cells, and Hep3B hepatic cancer cells) $M_4N$ induced cell death with UCN-01 at least either additively or weakly synergistically. In either case the combined drug treatment of $M_4N$ with UCN-01 improved the activity to induce tumor cell death over the single drug treatment of either $M_4N$ or UCN-01 alone.

Example 5

Figure 6A:
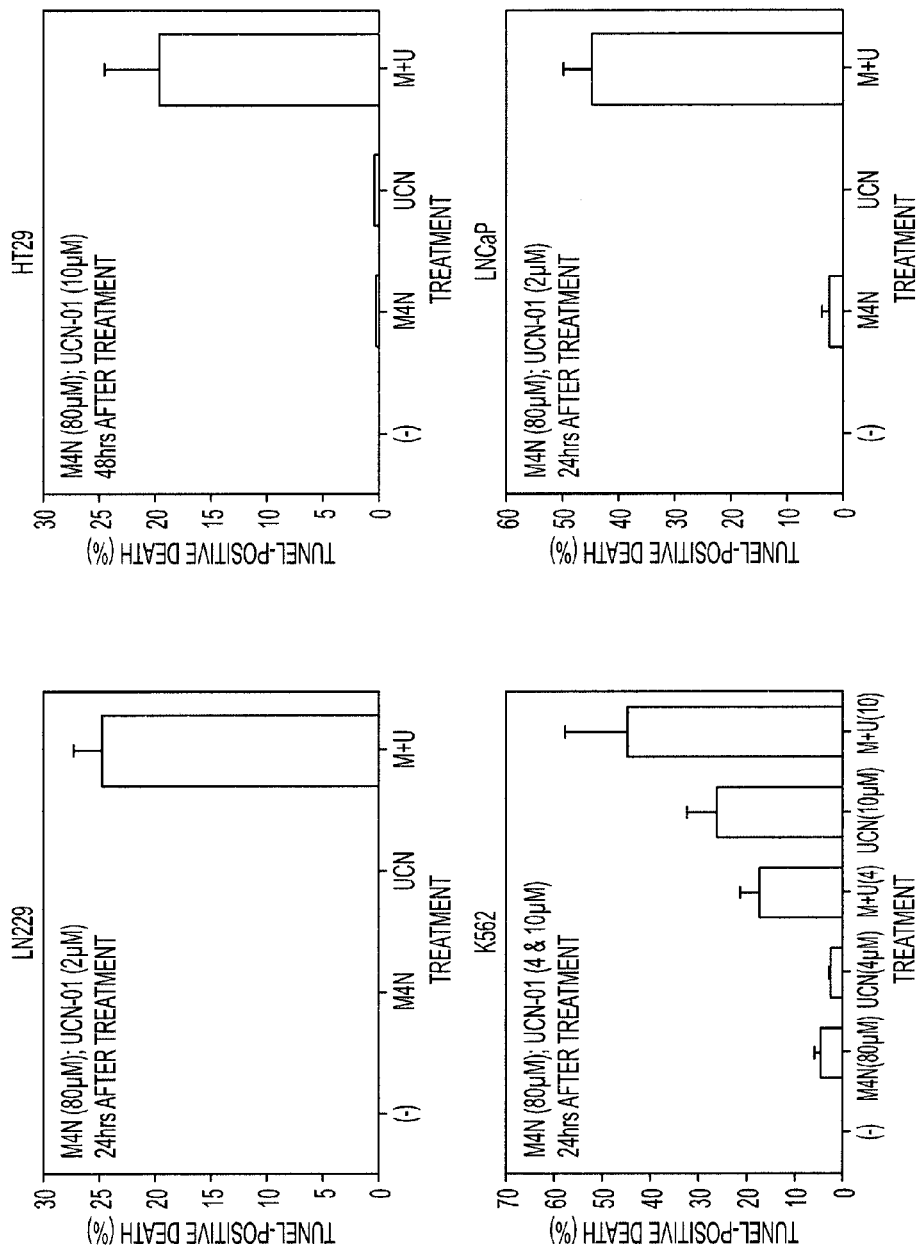
FIG. 6. TUNEL-positive cell death induced by M$_4$N/UCN-01 combination treatment in various cancer cell lines. The cell death was examined by TUNEL assay in various cancer cell lines treated with M$_4$N and UCN-01 for either 24 or 48 hrs. The concentration of M$_4$N is either 40 or 80 μM. The concentration of UCN-01 is 1, 2, 3, 4, 5, or 10 μM. The exact conditions are described inside each figure. Data are presented as means (+/−) SD in triplicates.
Figure 6B:
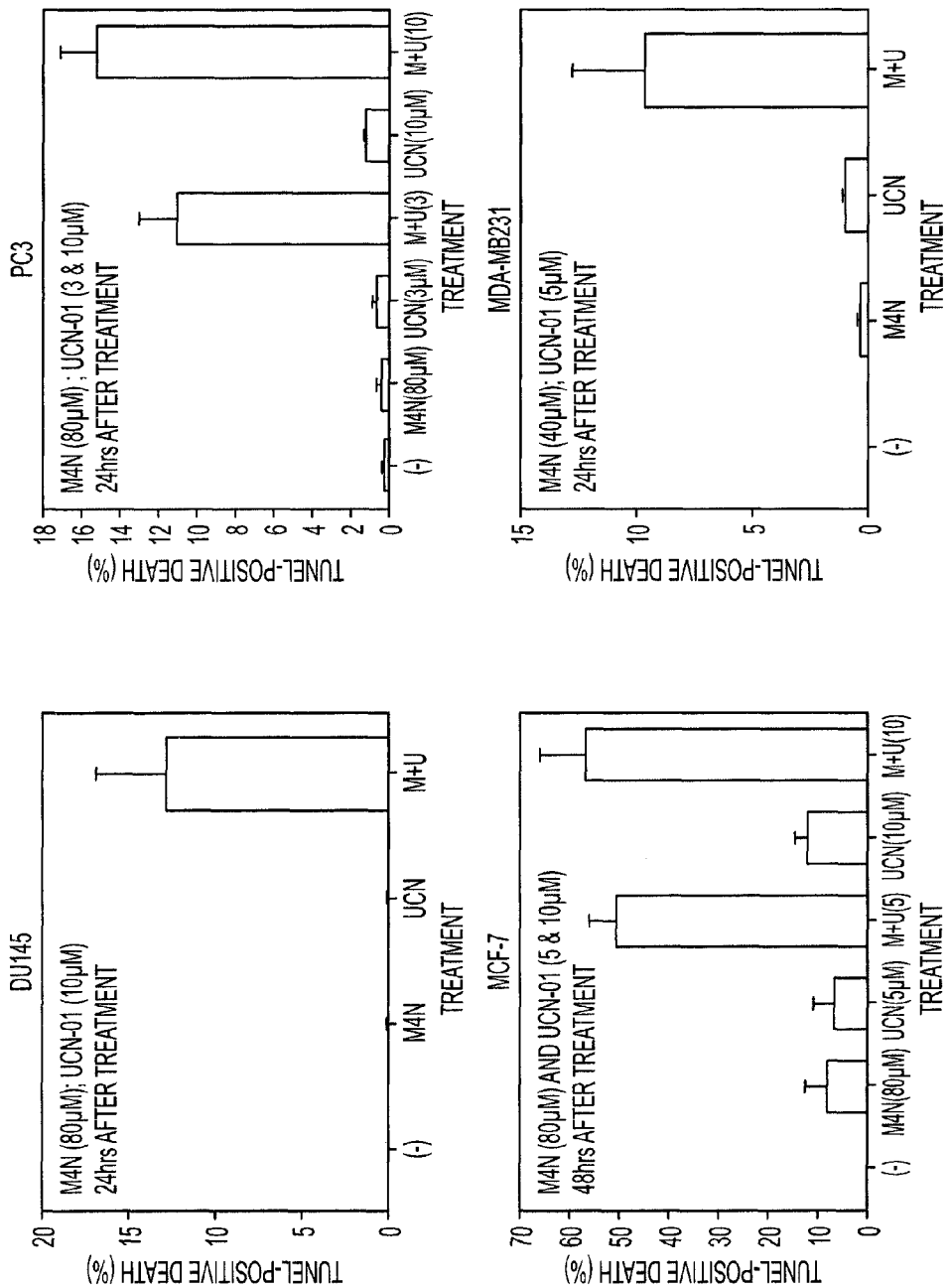
Figure 6C:
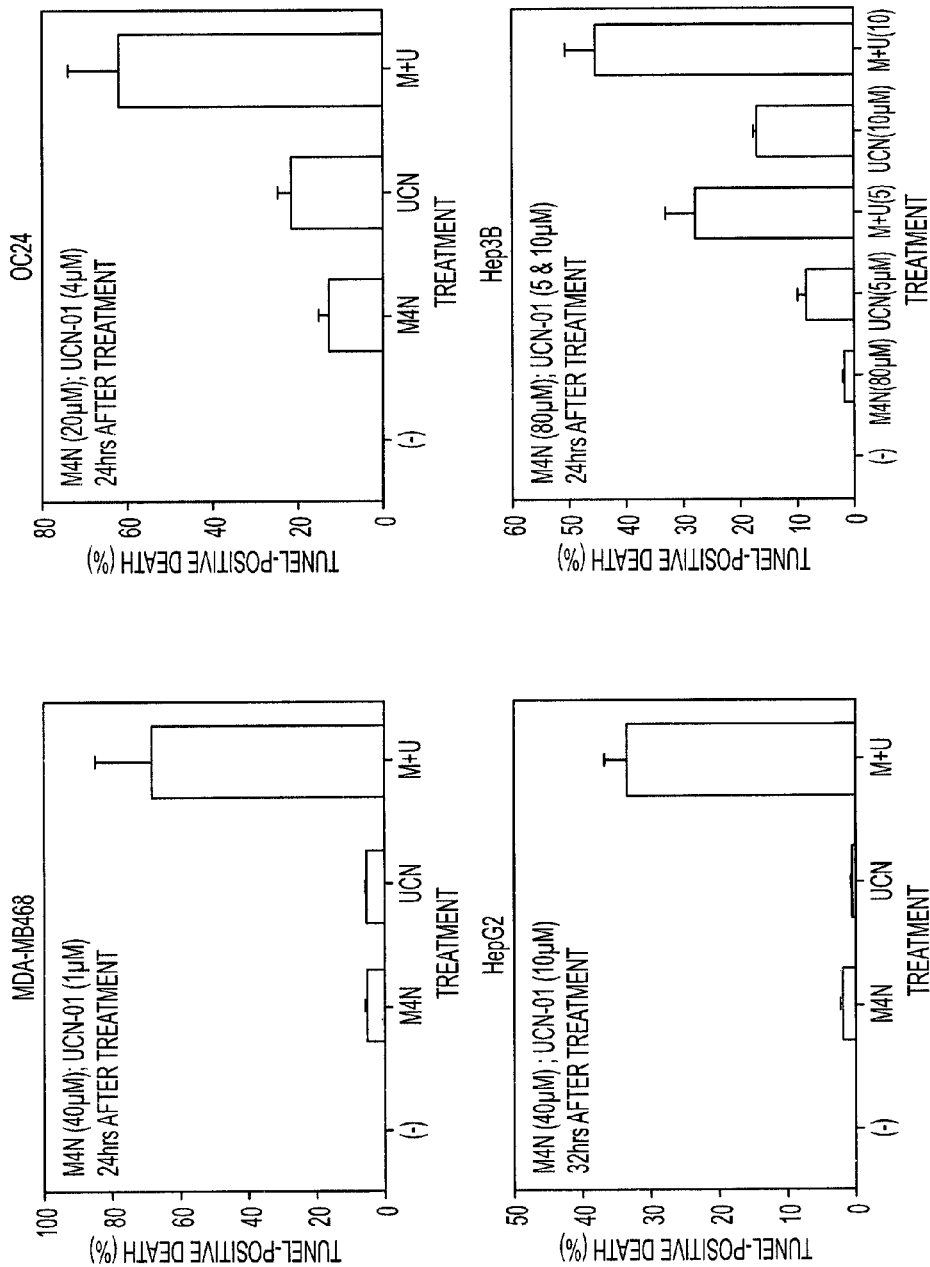
Figure 7:
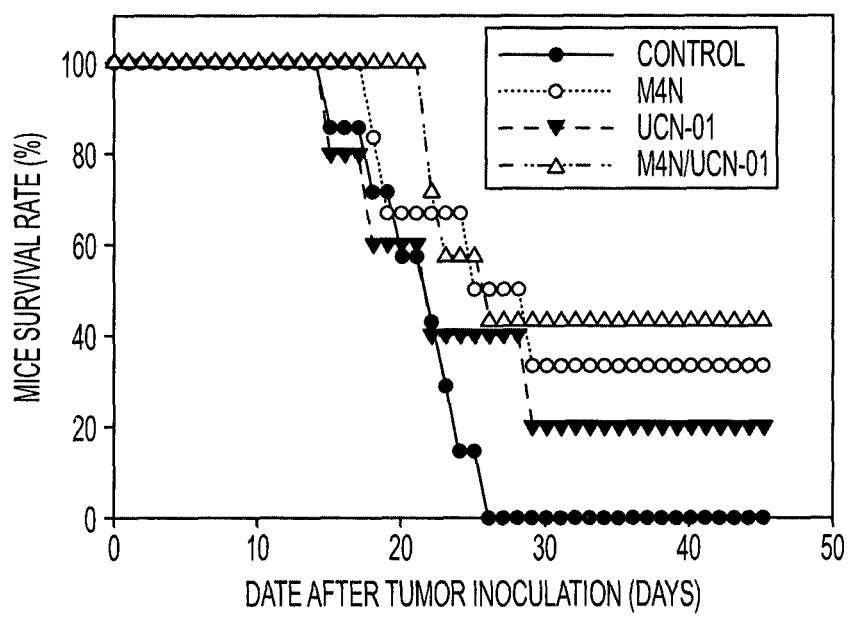
FIG. 7. Effect of M$_4$N/UCN-01 combination treatment on the survival rate of OC24 tumor-bearing nude mice T-cell deficient male nude mice (nu/nu) were intraperitoneally inoculated with 5×10$^4$ OC24 human ovarian cancer cells per mouse. Three days after tumor implantation the drug treatment started. The compounds were intravenously injected into the tail vein of mice at the daily dose of 0.1 ml per mouse. One shot of injections contains 1 mg of M$_4$N, 88.4 μg of UCN-01, 1 mg of M$_4$N and 88.4 μg of UCN-01, or the vehicle alone. The drug injections were performed once every day after day 3 until day 25 after tumor implantation. After this the drug injections were performed once every three days until day 35. The numbers of the mice used were 7, 6, 5, and 7 for the control, the M$_4$N, the UCN-01, and the combination treatment group respectively.

Effect of the Combination Treatment of $M_4N$ with UCN-01 on the Survival Rate of OC24 Ovarian Cancer-Bearing Mice The tissue culture data (FIG. 6) suggested that the combination treatment of $M_4N$ with UCN-01 had a potential to improve anticancer efficacy of $M_4N$ in a wide range of cancers. Next we examined if this combination treatment could improve the anticancer efficacy of $M_4N$ in animal experiments. In this experiment we used OC24 ovarian cancer-bearing nude mice as a model system. OC24 cells are very aggressive cancers and have the ability to kill essentially all the mice when only ten thousand cancer cells are inoculated intraperitoneally into a mouse. Since the tissue culture data (FIG. 1) showed that $M_4N$/UCN-01 combination treatment only additively improved cell death induction efficacy over either $M_4N$ or UCN-01 single treatment in this cell line, this animal experiment should reveal the potential of this combination treatment to improve anticancer efficacy under the least optimal conditions. The data for survival rate of OC24 ovarian cancer-bearing mice with or without drug treatment was shown in FIG. 7. All the mice without any treatments died in less than 26 days after the tumor inoculation. Meanwhile certain percentages of the mice survived in the all treatment groups ($M_4N$ alone, UCN-01 alone, or $M_4N$/UCN-01 combination) beyond 45 days after treatment (the time of preparation of the current manuscript). The survival rate at 45 days after treatment was 33%, 20%, and 42% for $M_4N$ alone, UCN-01 alone, or $M_4N$/UCN-01 combination group respectively. The data indicated that $M_4N$ and UCN-01 additively improved the efficacy of anticancer efficacy of each drug in this animal model, as expected from the tissue culture experiment (FIG. 6).

Effect of the Combination Treatment of $M_4N$ with UCN-01 on the Weight of Ascites Fluid and Abdominal Tumors in OC24 Ovarian Cancer-Bearing Mice.

Figure 8A:
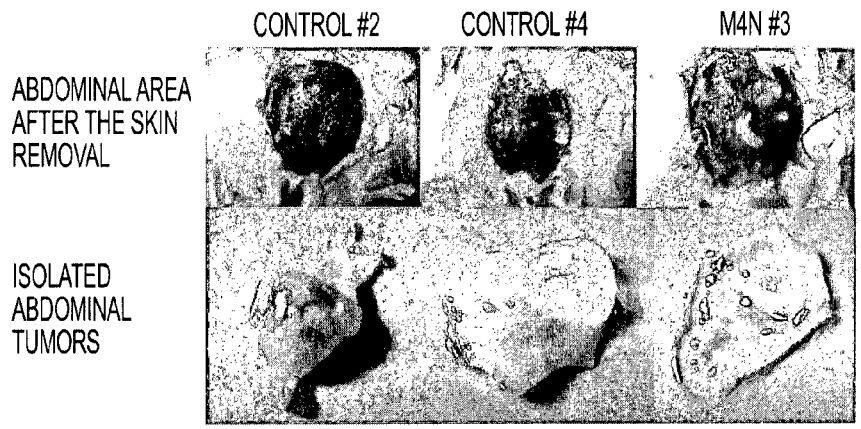
FIG. 8. Effect of M$_4$N/UCN-01 combination treatment on OC24 human ovarian cancer tumor-bearing mice in typical cases. A: Examples of abdominal tumors of which weights were measured to estimate the anticancer efficacy of M$_4$N/UCN-01. The actual numbers for tumor weight, ascites volume, and mouse weight in all the tumor-bearing mice that we examined are listed in Table I & II. Here the photos of solid abdominal tumors obtained from the mice in three typical cases (control #2 and #4 mice; M4N #3 mouse) are shown. Usually these sort of solid tumors are formed around the abdominal region where OC24 cells were originally inoculated into the peritoneum. B: Photos of the abdominal tumor in the #5 mouse treated with both M$_4$N and UCN-01. The photos of abdominal region of the #5 mouse which was treated with both M$_4$N and UCN-01 were taken at 22, 26, 29, 33, and 43 days after tumor inoculation. The solid abdominal tumor was indicated by a circle in black. C: Effect of M$_4$N/UCN-01 combination treatment on the ascites volume and the size of the abdominal tumor (shown in FIG. 8B above) in the #5 mouse treated with both M$_4$N and UCN-01.

The survival rate data (FIG. 7) indicates that $M_4N$/UCN-01 combination treatment had some beneficial effect to improve the anticancer efficacy of either $M_4N$ or UCN-01 to extend life-span of tumor-bearing mice. To further evaluate the anticancer efficacy of $M_4N$/UCN-01 combination treatment, we next measured the volume of the ascites fluid and that of abdominal tumors. The ascites fluid was collected from the peritoneal cavity at the time of death of tumor-bearing mice. Abdominal tumors are usually located in the vicinity of the area where the tumors were inoculated by the needle. FIG. 8A shows the pictures of typical abdominal tumors as examples. Table 1 shows the weight of ascites fluid and tumor weight at the time of death of the mice. The data was compiled at 45 days after tumor inoculation. Therefore there were still several mice who still survived from tumor burden. The data showed overall tendency that the weight of abdominal tumors were smaller in the mice treated with $M_4N$/UCN-01 combination treatment than in the control mice or in the mice treated with either $M_4N$ or UCN-01 alone.

TABLE I

Effect of $M_4N$/UCN-01 combination treatment on the weight of ascites fluid and abdominal tumors in OC24 tumor-bearing mice at the time of death.

| Drug | Weight of the Ascites Fluid (g) | Tumor Weight (mg) |
|---|---|---|
| Control | | |
| #1 | N/A | N/A |
| #2 | 6.3 | 400 |
| #3 | 9.3 | 561 |
| #4 | 7.1 | 100 |
| #5 | 6.7 | 34 |
| #6 | 4.8 | — |
| #7 | 11.2 | — |
| M4N | | |
| #1 | 4.4 | 101.3 |
| #2 | Living | — |
| #3 | 7.8 | <100 |
| #4 | Living | — |
| #5 | 5.8 | 360.5 |
| #6 | 16.1 | 69 |
| UCN-01 | | |
| #1 | 7.4 | No Tumor |
| #2 | 15 | 360.5 |
| #3 | Living | — |
| #4 | 14.3 | No Tumor |
| #5 | 2.9 | 87 |
| M4N + UCN-01 | | |
| #1 | 7.9 | No Tumor |
| #2 | 4.8 | 76 mg |
| #3 | Living | — |
| #4 | 14.9 | 47.3 |
| #5 | Living | — |
| #6 | Living | — |
| #7 | 11.2 | No Tumor |

The ascites fluid and abdominal tumors were collected at the time of death for each mouse. Since the data was obtained at 45 days after tumor inoculation, some mice were still alive and unavailable for measurement of the weight.

Once the ascites fluid starts to accumulate in the peritoneal cavity, it sometimes constitutes a significant portion of the body weight. Table II shows the change of the body weight of each mouse over the time after tumor inoculation.

TABLE II

Body weight change in OC24 tumor-bearing mice treated with M4N/UCN-01 drug combination.

| Day No. Injection | 10-Dec | 12-Dec | 13-Dec | 18-Dec | 22-Dec | 28-Dec | 1-Jan | 4-Jan | 5-Jan | 7-Jan | 8-Jan | 11-Jan | 12-Jan | 13-Jan | 14-Jan | 15-Jan | 16-Jan | 17-Jan | 18-Jan | 19-Jan | 20-Jan | 21-Jan | 22-Jan | 23-Jan |
|---|---|---|---|---|---|---|---|---|---|---|---|---|---|---|---|---|---|---|---|---|---|---|---|---|
| | 0 | 2 | 3 | 8 | 12 | 18 | 22 | 25 | 26 | 28 | 29 | 32 | 33 | 34 | 35 | 36 | 37 | 38 | 39 | 40 | 41 | 42 | 43 | 44 |
| | | | <------Daily------> | | | | | | ↑ | | | ↑ | | | | | | | | | | | | |
| Control | | | | | | | | | | | | | | | | | | | | | | | | |
| #1 | 23.9 | | | 22.6 | 23.6 | 30.3 | 29.6 (31st Dec) | | | | | | All Weights represented in grams | | | | | | | | | | | |
| #2 | 22 | | | 20.1 | 19.9 | 26.3 | 28.7 | | | | | | Control: 7/7 (100%) mice died. | | | | | | | | | | | |
| #3 | 21.6 | | | 20.6 | 21.2 | 23.3 | | | 30 | | 30.9 | | They lived for 23 to 30 days on an average. | | | | | | | | | | | |
| #4 | 21.6 | | | 21.1 | 21.6 | 24.2 | 29.7 (2nd Jan) | | | | | | Day 0 is taken as reference for injection of ovarian tumor cells. | | | | | | | | | | | |
| #5 | 23.5 | | | 23.4 | 23.6 | 25.4 | | 28.8 | 33 | | | | Day 8-(M + U) & UCN group were not recorded as the mice were very agitated. | | | | | | | | | | | |
| #6 | 22.1 | | | 20.7 | 21.7 | 22.6 | | | | Died | | | Weights in red represent body weight of dead mouse | | | | | | | | | | | |
| #7 | 22.7 | | | 21.8 | 20.4 | 24 | | | | | | | | | | | | | | | | | | |
| M4N | | | | | | | | | | | | | | | | | | | | | | | | |
| #2 | 24.1 | | | 22.3 | 22.8 | | 23.9 | | 23.2 | | 24.1 | | 26.2 | 25.5 | 25.3 | 25.3 | 24.8 | 25.7 | 25.8 | 25.9 | 26.3 | 26.4 | 26.4 | 25.3 |
| #4 | 22.9 | | | 20.8 | 21.2 | | 21.9 | | 21.5 | | 22.5 | | 22.7 | 22.5 | 23.1 | 22.9 | 22 | 22.4 | 22.6 | 22.9 | 22.7 | 22.9 | 23.1 | 23.2 |
| #1 | 23.5 | | | 22.9 | 23.4 | | 27.7 | 28 | 28 | | 28.1 | 27.9 | | | | | | | | | | | | |
| #3 | 22.3 | | | 21.5 | 20.9 | | 30.1 | 29.8 (31st Dec) | 29.8 (Euthanized on 1st Jan) | | | | | | | | | | | | | | | |
| #5 | 20 | | | 19.1 | 20.2 | | 25.8 (31st Dec) | | 38.8 | 37.5 | | | | | | | | | | | | | | |
| #6 | 21.4 | | | 20.9 | 20.5 | | 27.7 | | | | | | | | | | | | | | | | | |
| UCN-01 | | | | | | | | | | | | | | | | | | | | | | | | |
| #3 | 22.8 | | | 23.4 | | | 24.4 | | 24.8 | | 25.5 | | 27.9 | 27.6 | 27.4 | 27.5 | 26.5 | 27.2 | 27.3 | 27.1 | 27.4 | 27.4 | 27.8 | 26.7 |
| #2 | 22.1 | | | 21.8 | | | 30.7 | | 29.5 | | | | | | | | | | | | | | | |
| #4 | 23.4 | | | 22.9 | 22.6 | | 35.7 | | 39.5 | 38.4 (6th Jan) | | | | | | | | | | | | | | |
| #1 | 21.6 | | | 21.5 | 22.6 | | 30.5 | | 35.9 | Found badly decomposed on 7th Jan | | | | | | | | | | | | | | |
| #5 | 19.6 | | | 18.3 | | | 22.9 | | 26.2 | 27.3 | 27.3 | 22.5 | | | | | | | | | | | | |
| #6 | 20.6 | | | 20.9 | 20.8 | | 21.9 Died due to injection & not the tumor (28th Dec) | | | | | | | | | | | | | | | | | |
| M4N + UCN-01 | | | | | | | | | | | | | | | | | | | | | | | | |
| #3 | 20.9 | | | 19.1 | 19.2 | | 20.9 | | 20.3 | | 21 | 22.5 | 23.1 | 23.4 | 23.5 | 23.4 | 19 | 17.4 | 21.9 | 22.1 | 22.7 | 22.9 | 22.8 | 22.7 |
| #5 | 23.7 | | | 23.6 | | | 30.5 | | 25.7 | | 25.5 | 27.7 | 27.2 | 28.4 | 27.6 | 28.2 | 26.6 | 28.1 | 28.1 | 27.9 | 28 | 28.6 | 28.5 | 27.7 |
| #6 | 21.9 | | | 20.3 | 20.3 | | 26 | | 23.4 | | 23 | 24 | 24.8 | 24.3 | 24.2 | 23.8 | 22.3 | 23.6 | 23.8 | 23.4 | 24 | 24.8 | 24.9 | 25 |
| #1 | 22.8 | | | 20.3 | 20.3 | | 30.7 | 31.8 | | | | | | | | | | | | | | | | |
| #2 | 23.8 | | | 21.2 | 21.2 | | 28.6 | | 27.5 | | 35.7 | | | | | | | | | | | | | |
| #4 | 20.8 | | | 21 | 21 | | 24.9 | | 32.5 | | | | | | | | | | | | | | | |
| #7 | 21.2 | | | 21.8 | 21.8 | | 22.7 | 32.4 | | | | | | | | | | | | | | | | |

The body weight was measured periodically for the mice treated with the vehicle alone, M4N alone, UCN-01 alone, or M4N/UCN-01 combination.
The precise conditions of drug injection protocols are described in the legend of FIG. 2. The #6 mouse in the UCN-01 group was accidentally killed. Therefore this mouse is omitted for the analysis of the data in FIG. 2-4, and Table I. Body weight is depicted in the scale of gram.

Figure 8B:
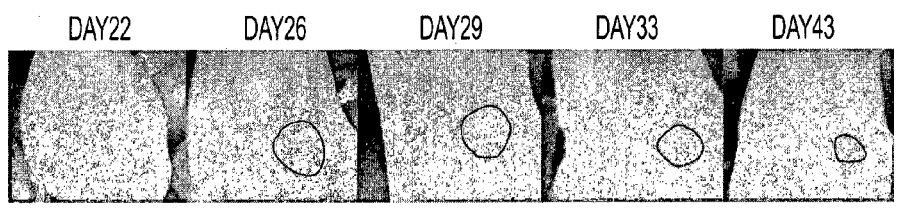
Figure 8C:
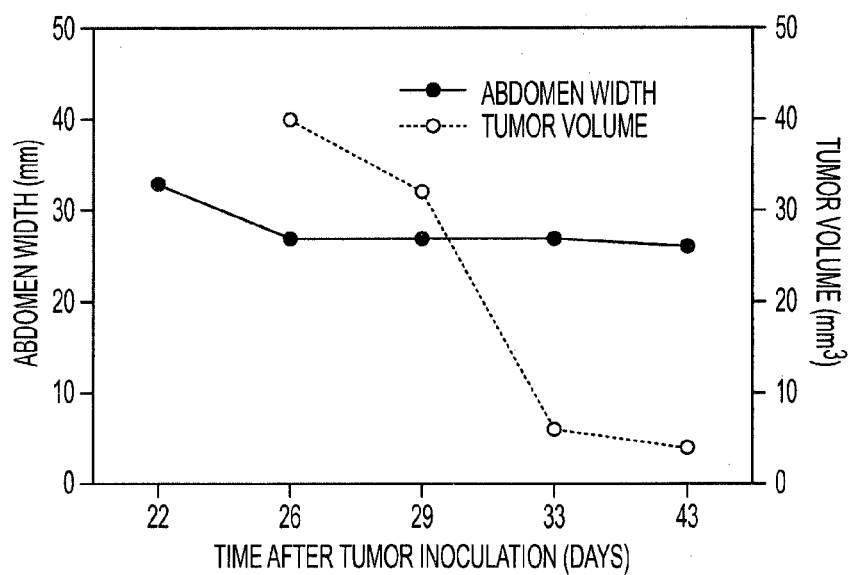

The increase of the body weight of deceased mice at the time of the death over the initial weight was 37.8% (SD=18.9%, N=19) while the increase of the body weight of alive mice at days after tumor inoculation over the initial weight was 9.5% (SD=7.5%, N=6). The difference of two groups is statistically significant by t-test (0.2%). This indicated that the body weight of the mice (or ascites fluid) increased very significantly at the time of their death. Therefore the body weight change can be used as an indicator to estimate the volume of ascites and thus overall condition of the mice. Table 2 shows that the body weight of the mouse #5 of the combination treatment group decreased from 30.5 g (day 22) to 25.7 g (day 26). The body weight increased slightly after day 26. However it hasn't reached the peak weight achieved at day 22 (30.5 g). FIG. 8B shows the pictures of this mouse from day 22 to day 43. The pictures show the apparent decrease of the volume of abdominal area from day 22 to day 29 through day 26. This almost certainly indicated the reduction of ascites fluid. The pictures also show that the size of subcutaneous tumor at the left center of abdominal area has been reduced from day 22 to day 43. The abdominal width indicative of the volume of ascites fluid, and the size of the abdominal tumor of this particular mouse was measured and plotted against the time after tumor inoculation (FIG. 8C), which clearly shows that the abdominal size and the tumor size decreased over the course of the time. The observations depicted in FIGS. 8 B and 8C indicate that the combination treatment of $M_4N$ with UCN-01 can suppress tumor burden even after the tumor size has already reached to a certain extent.

Discussion

Autophagy is a crucial cellular process to mitigate the damages to the cells under stress (27, 28). Autophagy can function in two opposite ways in terms of cancer therapy (27, 28). Stress activates autophagy, which mitigates damage and promotes senescence, which limits tumorigenesis. On the other hand autophagy also enables tumor cells to survive metabolic stress, become dormant, and regenerate with stress relief that can promote tumorigenesis. Cytotoxic, targeted, and radiation therapy amplifies stress and autophagy, in addition to the inherent metabolic stress in the tumor microenvironment. Autophagy inhibitors block autophagy, which amplifies damage and cell death, while also impairing dormancy and regeneration, tilting the balance in favor of tumor regression. Alternatively, autophagy stimulators may be useful for cancer prevention by enhancing damage mitigation and senescence.

However, overall the recent literatures indicated that the inhibition of autophagy is practically beneficial to improve anticancer drug effects. Amaravadi et al. showed that the inhibition of autophagy by hydroxychloroquine (HCQ), which blocks lysosome acidification and autophagosome degradation, improved the anticancer efficacy of alkylating drugs (47). Ding et al. showed that the induction of autophagy by the chemicals such as A23187, tunicamycin, thapsigargin, and brefeldin A mitigated stress for colon cancer cell lines and protected them from cell death while autophagy induced by the same chemicals did not confer protection in a normal colon cell lines and in the non-transformed embryonic fibroblasts but rather contributed to cell death (48). These findings indicated that autophagy inhibition induced by HCQ could augment anticancer therapy-mediated cell death specifically in cancer cells. A number of clinical trials have been initiated in patients with solid and hematopoietic tumors to test this theory (27). Most of these trials are combinations of HCQ with cytotoxic chemotherapy, inducers of metabolic stress or targeted therapies with the overall hypothesis that autophagy is a mechanism of therapeutic resistance, and HCQ will increase cytoxicity by abrogation of autophagy.

In response to metabolic stress, autophagy can delay cell death by apoptosis, and in apoptotic-defective cells, inactivation of the autophagy survival pathway promotes necrotic cell death in vitro and in tumors in vivo (29, 31,36) We found that $M_4N$ blocks autophagy (this observation was demonstrated by the reduction of net flow of LC3B-II protein with both western blotting and immunocytochemistry). Although HCQ is already established as an inhibitor for autophagy, the mechanism to suppress autophagy seems to be different between $M_4N$ and HCQ. Unlike HCQ, the target of $M_4N$ seems to be BNIP3 protein, which is an activator for both cell death and autophagy. For instance BNIP3 was shown to mediate autophagy induced by hypoxic stress and protect cells from hypoxia-mediated cell injuries (24). Tumors are often exposed to hypoxic conditions because fast growing tumors usually don't get enough blood vessel supplies. At the same time cytotoxic, targeted, and radiation therapy amplifies stress. The prevention of BNIP3 expression will reduce the ability for cancer cells to cope with these stresses often accompanied with tumor development and cancer therapy.

Other than the effect to promote autophagy, BNIP3 is known to induce mitochondrial membrane depolarization and activate cytochrome c-capsapse-9-caspase-3 apoptotic pathway (25, 26). The reduced BNIP3 expression should result in mitochondrial membrane hyperpolarization, which blocks the activation of caspase-9 and 3 induced by other anticancer drugs. In this sense BNIP3 inhibition by $M_4N$ should block both autophagy and conventional mitochondria-mediated cell death. In fact caspase-9 and 3 activation induced by UCN-01 treatment was interfered in by the concomitant treatment of UCN-01 with $M_4N$ (FIG. 1C). $M_4N$ was shown to hyperpolarize mitochondrial membrane potential, which should interfere in the functions of mitochondria-related cell death mechanisms. We also found that the depolarization of mitochondrial membrane potential induced by the treatment with either rottlerin or Ly294002 in LNCaP cells was reversed to the normal potential to some extent by the concomitant treatment of these chemicals with $M_4N$ (see addendum). The data overall indicates that BNIP3 inhibition induced by $M_4N$ blocks mitochondria-related cell death mechanism as much as it suppresses autophagy.

Interestingly there is a Sp1 consensus sequence in the promoter region of BNIP3 protein (49). One of the mechanisms for $M_4N$ to perform diverse physiological activities is the reversible inhibition of Sp1 protein to bind Sp1 consensus sequences of the genome (3). It is quite possible that $M_4N$ suppressed BNIP3 expression by reducing promoter activity of BNIP3 gene through binding to the Sp1 consensus sequence of the promoter. Recently it was shown that M4N was able to reduce inflammation through its ability to bind to NFκB consensus binding sequence site (50). They showed that since there is a homology between consensus sequence of Sp1 binding site and that of NFκB binding site, M4N was able to bind to bind both Sp1 and NFκB sites (50). Several papers have been published indicating that NFκB plays a major role in the regulation of BNIP3 expression (51, 52). These findings suggested that M4N might interfere in BNIP3 expression by binding to NFκB consensus sequence rather than Sp1 consensus sequence in the BNIP3 promoter.

Regardless of the blockage of mitochondrial cell death mechanisms, the combination treatment of $M_4N$ with other anticancer drugs (and also with rottlerin or Ly294002, see addendum) definitely improved the anticancer efficacy of these anticancer drugs. This is the case because the combination treatment seems to be able to utilize other cell death mechanisms than conventional mitochondria-related cell death mechanisms. Caspase-7-related cell death pathway is one of the cell death machineries which are allowed to be used by the combination treatments since caspase-7 activation does not require mitochondrial activation (53, 54). The study with the western blotting, calorimetric assay, and zDEVD-fmk inhibitor experiments indicates that caspase-7 is responsible for the cell death induced by the combination treatments to some degrees. There are many literatures indicating that caspase-7 activation is responsible for cell death induction in cancer cells under some experimental conditions as well (55, 56), which supports our findings that caspase-7 activation is capable of inducing cell death which is sufficient enough to cause effective anticancer activity. Since zDEVD-fmk cannot inhibit cell death completely (FIG. 1E), probably caspase-independent cell death mechanisms (such as necrosis) participate in the cell death induced by the combination treatments as well (57). The study using zVAD-fmk in the experimental system for LNCaP cells treated with the combination treatments of $M_4N$ with rottlerin and Ly294002 also supports this concept (see addendum). Previously it was shown that the consequence of zVAD inhibition of both cell death (through inhibition of caspases) and cell survival by autophagy (through inhibition of Cathepsin B) is induction of necrotic cell death (58). Since M4N can block both conventional mitochondria-related cell death and autophagic cell survival, M4N treatment should be capable of induction of necrosis if their findings will be applied to our result.

Anticancer drugs have adverse effect on normal tissues as much as on cancer cells. In many cases there are substantial differences in mitochondrial physiology between normal cells and cancer cells. To maintain high energy consumption because of high growth rate, mitochondria in cancer cells are often in the condition of membrane hyperpolarization (13, 14). Mitochondria-mediated cell death mechanisms are usually blocked in hyperpolarized mitochondria. This makes cancer cells resistant to cell death stimuli. On the other hand, normal cells are very susceptible to cell death stimuli since normal mitochondria easily start to undergo membrane depolarization responding to those stimuli. LNCaP cells are usually considered to be less aggressive than many other cancer cells since LNCaP cells are wild type p53 positive and androgen receptor positive. If this assumption is correct, the difference in the expression of cleaved forms of caspase-9 and -3 between LNCaP cells (FIG. 1C) and the cells such as MCF-7 or HepG2 cells (FIG. 4C) is considered to be related to the difference of the physiology of mitochondria between normal cells and cancer cells to some degree. Then the western blotting data showing the interference of activation of caspase-9 and -3 by $M_4N$ (FIG. 1C) can be applied to what would happen to mitochondria-related cell death mechanisms of normal tissues treated with $M_4N$, which is that $M_4N$ should be able to protect normal cells from adverse toxic effects of anticancer drugs by preventing conventional mitochondria-related cell death. Meanwhile $M_4N$ still allows caspase-7-dependent cell death and other mitochondria-independent cell death. Then overall result of the combination treatment with $M_4N$ should be that there will be more toxicity towards cancer cells with less toxicity towards normal cells.

Cancer cells which are more energy hungry than normal cells are more vulnerable towards metabolic stress than normal cells. Autophagic blockage induced by $M_4N$ causes more detrimental effects towards cancer cells than normal cells and increases the efficacy of anticancer drugs in cancer cells while BNIP3 inhibition induced by $M_4N$ protects normal cells from toxic drug effects resulted from caspase-9 and -3-dependent cell death which is more detrimental towards normal cells than cancer cells (because cancer cells often have broken mitochondria while normal cells have fully functional mitochondria). Probably this is the main reason why $M_4N$ is fairly nontoxic, which has been proven in many ways in clinical trials for $M_4N$ using human patients (10). It might be the case that patients can tolerate with higher dosage of anticancer drugs in the combination treatments with $M_4N$, since it is reasonable to predict that $M_4N$ reduces toxic effects of other anticancer drugs by preventing conventional cell death mechanism.

When autophagic blockage and BNIP3 blockage works together in the presence of anticancer drugs with strong efficacy to destabilize integrity of cellular systems, the consequence is that cancer cells are induced to cell death more efficiently while normal cells are fairly protected from strong cytotoxic effects from anticancer drugs. $M_4N$ is very unique in a sense that one chemical agent can do these two very important actions essential for enabling combined anticancer drugs to work efficiently in clinical settings. Additionally the finding that $M_4N$ inhibits BNIP3 activity enlarges the potential usage of $M_4N$ beyond the usage as an anticancer drug. BNIP3 is considered to be a major cause of cardiac cell death after cardiac infarction (26). Since $M_4N$ can alleviate caspase-dependent cell death through BNIP3 activation, it will protect remaining cardiac cells from dying after cardiac infarction. This scheme can work in many other situations where there is a need to protect cells from dying under the emergency.

REFERENCES

1. Hwu, J. R., W. N. Tseng, J. Gnabre, P. Giza, P, and R. C. Huang. 1998. Antiviral activities of methylated nordihydroguaiaretic acids. 1. Synthesis, structure identification, and inhibition of tat-regulated HIV transactivation. J. Med. Chem. 41:2994-3000.
2. Chen, H., L. Teng, J. N. L1, R. Park, D. E. Mold, J. Gnabre, J. R. Hwu, W. N. Tseng, and R. C. Huang. 1998. Antiviral activities of methylated nordihydroguaiaretic acids. 2. Targeting helpes simplex virus replication by the mutation insensitive transcription inhibitor tetra-O-methyl-NDGA. J. Med. Chem. 41:3001-3007.
3. Heller, J. D., J. Kuo, T. C. Wu, W. M. Kast, and R. C. Huang. 2001. Tetra-O-methyl nordihydroguaiaretic acid induces G2 arrest in mammary cells and exhibits tumoricidal activity in vivo. Cancer Res. 61:5499-5504.
4. Chang, C. C., J. D. Heller, J. Kuo, and R. C. Huang. 2004. Tetra-O-methyl nordihydroguaiaretic acid induces growth arrest and cellular apoptosis by inhibiting Cdc2 and surviving expression. Proc. Natl. Acad. Sci. U.S.A. 101: 13239-13244.
5. Park, R., C. C. Chang, Y. C. Liang, Y. Chung, R. A. Henry, E. Lin, D. E. Mold, and R. C. Huang. 2005. Systemic treatment with tetra-O-methyl nordihydroguaiaretic acid suppresses the growth of human xenograft tumors. Clin. Cancer Res. 11:4601-4609.
6. Wang, L., Wei, D., Huang, S., Peng, Z., Le, X., Wu, T. T., Yao, J., Adjani, J, and Xie, K. 2003. Transcription factor Sp1 expression is a significant predictor of survival in human gastric cancer. Clin. Cancer Res. 9: 6371-80.
7. Yao, J. C., Wang, L., Wei, D., Gong, W., Hassan, M, Wu, T. T., Mansfield, P., Ajani, J., and Xie, K. 2004. Association between expression of transcription factor Sp1 and increased vascular endothelial growth factor. Clin. Cancer Res. 10: 4109-17.
8. The data from a clinical trial: Study of Intralesional Injection of M4N in Patients with Refractory Malignant Tumors of the Head and Neck. ClinicalTrials. gov identifier: NCT00057512, (http://clinicaltrials.gov/ct2/show/NCT00057512?term=em 1421&rank=6).

9. N. Khanna, R. Dalby, M. Tan, S. Arnold, J. Stern, and N. Frazer. 2007. Phase I/II clinical safety studies of terameprocol vaginal ointment. Gynecologic Oncology 107: 554-562.

10. The data from a clinical trial: Tetra-O-methyl Nordihydroguaiaretic acid in treating patients with recurrent high-grade glioma. ClinicalTrials.gov identifier: NCT00404248, (http://clinicaltrials.gov/ct2/show/NCT00404248?term=M4N&rank=5).

11. Omuro, A. M. 2008. Exploring multi-targeting strategies for the treatment of gliomas. Curr. Opin. Investig. Drugs. 9: 1287-95.

12. Baxevanis, C. N., Perez, S. A., and Papamichail, M. 2009. Combinatorial treatments including vaccines, chemotherapy and monoclonal antibodies for cancer therapy. Cancer Immunol. Immunother. 58: 317-24.

13. Michelakis, E. D., Sutendra, G., Dromparis, P., Webster, L., Haromy, A., Niven, E., Mguire, C., Gammer, T.-L., Mackey, J. R., Fulton, D, Abdulkarim, B., McMurtry, M. S., and Petrunk. K. C. Metabolic Modulation of Glioblastoma with Dichloroacetate. Sci. Transl. Med. 2: 31-4.

14. Mockenbery, D. M. 2010. Targeting mitochondria for cancer therapy. 51: 476-89.

15. Gamido, C., Galluzzi, L., Brunet, M., Puig, P. E., Didelot, C., and Kroemer, G. 2006. Mechanisms of cytochrome c release from mitochondria. Cell Death Differ. 13: 1423-33.

16. Martinez-Caballero, S., Dejean, L. M., Jonas, E. A., and Kinnally, K. W. 2005. The role of the mitochondrial apoptosis induced channel MAC in cytochrome c release. J. Bioenerg. Biomembr. 37: 155-64.

17. Tait, S. W. and Green, D. R. 2010. Mitochondria and cell death: outer membrane permeabilization and beyond. Nat. Rev. Mol. Cell. Biol. 11: 621-32.

18. Leber, B., Geng, F., Kale, J., and Andrews, D. W. 2010. Drugs targeting Bcl-2 family members as an emerging strategy in cancer. Expert Rev. Mol. Med. 12:e28.

19. Kang, M. H., and Reynolds, C. P. 2009. Bcl-2 inhibitors: targeting mitochondrial apoptotic pathways in cancer therapy. Clin. Cancer Res. 15: 1126-32.

20. Chonghaile, T. N. and Letai, A. 2008. Mimicking the BH3 domain to kill cancer cells. Oncogene. Supple 1:S149-57.

21. Garcia-Saez, A. J., Fuertes, G., Suckale, J., and Salgado, J. 2010. Permeabilization of the outer mitochondrial membrane by Bcl-2 proteins. Adv. Exp. Med. Biol. 677: 91-105.

22. Burton, T. R., and S. B. Gibson. 2009. The role of Bcl-2 family member BNIP3 in cell death and disease: NIPping at the heels of cell death. Cell Death Diff. 16:515-23.

23. Zhang, F., and P. A. Ney. 2009. Role of BNIP3 and NIX in cell death, autophagy, and mitophagy. Cell Death Diff. 16: 939-46

24. Zhang, H., M. Bosch-Marce, L. A. Shimoda, Y. S. Tan, J. H. Baek, J. B. Wesley, F. J. Gonzalez, and G. L. Semenza. 2008. Mitochondrial Autophagy Is an HIF-1-dependent Adaptive Metabolic Response to Hypoxia. J. Biol. Chem. 283:10892-903.

25. Kubli, D. A., Ycaz, J. E., and Gustafsson, A. B. 2007. Bnip3 mediates mitochondrial dysfunction and cell death through Bax and Bak. Biochem. J. 405: 407-15.

26. Quinsay, M. N., Lee, Y., Rikka, S. Sayen, M. R., Molkentin, J. D., Gottlieb, R. A., and Gustafsson, A. B. 2010. Bnip3 mediates permeabilization of mitochondria and release of cytochrome c via a novel mechanism. J. Mol. Cell. Cardiol. 48: 1146-56.

27. White, E. and R. S. DiPaola. 2009. The Double-Edged Sword of Autophagy Modulation in Cancer. Clin. Cancer Res. 15: 5308-16.

28. Maiuri, M. C., E. Tasdemir, A. Criollo, E. Morselli, J. M. Vicencio, R. Carnuccio, and G. Kroemer. 2009. Control of autophagy by oncogenes and tumor suppressor genes. Cell Death Diff. 16: 87-93.

29. Degenhardt, K., Mathew, R., Beaudoin, B., Bray, K., Anderson, D., Chen, G., Mukherjee, C., Shi, Y., Gellnas, C., Fan Y., Nelson, D. A., Jin, S., and White, E. 2006. Autophagy promotes tumor cell survival and restricts necrosis, inflammation, and tumorigenesis. Cancer Cell 10: 51-64.

30. Hara, T., Nakamura, K., Matsui, M., Yamamoto, A., Nakahara, Y., Suzuki-Migishima, R., Yokoyama, M., Mishima, K., Saito, I., Okano, H., and Mizushima, N. 2006. Suppression of basal autophagy in neural cells causes neurodegenerative disease in mice. Nature 441: 885-9.

31. Karantza-Wadsworth, V., Patel, S., Kravchuk, O., Chen, G., Mathew, R., Jin, S., and White, E. 2007. Autophagy mitigates metabolic stress and genome damage in mammary tumorigenesis. Genes Dev. 21: 1621-35.

32. Komatsu, M., Waguri, S., Chiba, T., Murata, S., Iwata, J., Tanida, I., Ueno, T., Koike, M., Uchiyama, Y., Kominami, E., and Tanaka, K. 2006. Loss of autophagy in the central nervous system causes neurodegeneration in mice. Nature 441: 880-4.

33. Komatsu, M., Waguri, S., Koike, M., Sou, Y. S., Ueno, T., Hara, T., Mizushima, N., Iwata, J., Ezaki, J., Murata, S., Hamazaki, J., Nishito, Y., Iemura, S., Natsume, T., Yanagawa, T., Uwayama, J., Warabi, E., Yoshida, H., Ishii, T., Kobayashi, A., Yamamoto, M., Yue, Z., Uchiyama, Y., Kominami, E., and Tanaka, K. 2007. Homeostatic levels of p62 control cytoplasmic inclusion body formation in autophagy-deficient mice. Cell 131: 1149-1163.

34. Kuma, A., Hatano, M., Matsui, M., Yamamoto, A., Nakaya, H., Yoshimori, T., Ohsumi, Y., Tokuhisa, T., and Mizushima, N. 2004. The role of autophagy during the early neonatal starvation period. Nature 432: 1032-6.

35. Lum, J. J., Bauer, D. E., Kong, M., Harris, M. H., Li, C., Lindsten, T., and Thompson, C. B. 2005. Growth factor regulation of autophagy and cell survival in the absence of apoptosis. Cell 120: 237-48.

36. Mathew, R., Kongara, S., Beaudoin, B., Karp, C. M., Bray, K., Degenhardt, K., Chen, G., Jin, S., and White, E. 2007. Autophagy suppresses tumor progression by limiting chromosomal instability. Genes Dev. 21: 1367-81.

37. Levine B, Kroemer G. 2008. Autophagy in the pathogenesis of disease. Cell 132: 27-42.

38. Mathew, R., Karantza-Wadsworth, V., and White, E. 2007. Role of autophagy in cancer. Nat. Rev. Cancer 7: 961-7.

39. Lopez, R. A., A. B. Goodman, M. Rhodes, J. A. Blomberg, and J. Heller. 2007. The anticancer activity of the transcription inhibitor terameprocol (meso-tetra-O-methyl nordihydroguaiaretic acid) formulated for systemic administration. Anti-Cancer Drugs 18:933-939.

40. Chou, T.-C. and Talalay, P. Quantitative analysis of dose-effect relationships: The combined effects of multiple drugs or enzyme inhibitors. Adv. Enz. Regul. 22: 27-55, 1984.

41. Wang, X., Z. Zili, J. Geller, and R. M. Hoffman. 1999. High-malignancy orthotopic nude mouse model of human prostate cancer LNCaP. The Prostate 39:182-186.

42. Bissery, M. C., Guenard, D., Gueritte-Voegelein, F., and Lavelle, F. 1991. Experimental antitumor activity of Taxotere (RP 56976, NSC 628503), a Taxol analogue. Cancer Res. 51: 4845-52.
43. L1, T. K. and L. F. Liu. 2001. Tumor cell death induced by topoisomerase-targeting drugs. Ann. Rev. Pharmacol. Toxicol. 41:53-77.
44. Huang, S., M.-A. Bjornsti, and P. J. Houghton. 2003. Rapamycins: Mechanism of Action and Cellular Resistance. Cancer Biology & Therapy 2:222-232.
45. Akinaga, S., K. Sugiyama, and T. Akiyama. 2000. UCN-01 (7-hydroxystaurosporine) and other indolocarbazole compounds: a new generation of anti-cancer agents for the new century?Anticancer Drug Des. 15:43-52.
46. Rubinsztein, D. C., A. M. Cuervo, B. Ravikumar, S. Sarkar, V. Korolchuk, S. Kaushik, and D. J. Klionsky. 2009. In search of an "autophagomometer" Autophagy 5: 585-589.
47. Amaravadi. R. K., D. Yu, J. J. Lum, T. Bui, M. A. Christophorou, G. I. Evan, A. Thomas-Tikhonenko, and C. B. Thompson. 2007. Autophagy inhibition enhances therapy-induced apoptosis in a Myc-induced model of lymphoma. J. Clin. Invest. 117:326-336.
48. Ding, W.-X., H.-M. Ni, W. Gao, Y.-F. Hou, M. A. Melan, X. Chen, D. B. Stolz, Z.-M. Shao, and X.-M. Yin. 2007. Differential Effects of Endoplasmic Reticulum Stress-induced
Autophagy on Cell Survival. J. Biol. Chem. 282: 4702-10.
49. Tracy, K., B. C. Dibling, B. T. Spike, J. R. Knabb, P. Schumacker, and K. F. Macleod. 2007. BNIP3 Is an RB/E2F Target Gene Required for Hypoxia-Induced Autophagy. Mol. Cell. Biol. 27: 6229-42.
50. Eads, D., R. L. Hansen, A. O. Oyegunwa, C. E. Cecil, C. A. Culver, F. Scholle, I. T. D. Petty, and S. M. Laster. 2009. Terameprocol, a methylated derivative of nordihydroguaiaretic acid, inhibits production of prostaglandins and several key inflammatory cytokines and chemokines. J. Inflamm. 6: 2-19.
51. Shaw, J. N. Yurkova, T. Zhang, H. Gang, F. Aguilar, D. Weidman, C. Scramstad, H.
Weisman, and L. A. Kirshenbaum. 2008. Antagonism of E2F-1 regulated Bnip3 transcription by NF-κB is essential for basal cell survival. Proc. Nat. Acad. Sci. USA. 105: 20734-9.
52. Shaw, J., T. Zhang, M. Rzezutek, N. Yurkova, D. Baetz, J. R. Davie, and L. A. Kirshenbaum. 2006. Transcriptional silencing of the death gene BNIP3 by cooperative action of NF-kB and histone deacetylase 1 in ventricular myocytes. Circ. Res. 99: 1347-54.
53. Lamkanfi, M., Kanneganti, T.-D., Damme, P. V., Berghe, T. V., Vanoverberghe, I., Vandekerckhove, J., Vandenabeele, P., Gevaert, K. and Nunez, G. 2008. Targeted peptidecentric proteomics reveals caspase-7 as a substrate of caspase-1 inflammasomes. Mol. Cell. Proteomics 7: 2350-63.
54. Gafni, J., Cong, X., Chen, S. F., Gibson, B. W., and Ellerby, L. M. 2009. Calpain-1 cleaves and activates caspase-7. J. Biol. Chem. 284: 25441-9.
55. Marcelli, M., R. G. Cunningham, S. Joe Haidacher, S. J. Padayatty, L, Sturgis, C. Kagan, and L. Denner. 1998. Caspase-7 is activated during lovastatin-induced apoptosis of the prostate cancer cell line LNCaP. Cancer Res. 58: 76-83.
56. Rokhlin, O. W., R. A. Glover, and M. B. Cohen. 1998. Fas-mediated apoptosis in human prostatic carcinoma cell lines occurs via activation of caspase-8 and caspase-7. Cancer Res. 58: 5870-5.
57. Kroemer, G. and Martin S. J. 2005. Caspase-independent cell death. Nature Med. 11: 725-30.
58. Wu Y T, Tan H L, Huang Q., Kim, Y. S., Pan, N., Ong, W. Y., Liu, Z. G., Ong, C. N. and Shen, H. M. 2008. Autophagy plays a protective role during zVAD-induced necrotic cell death. Autophagy 4: 457-66.

We claim:
1. A synergistic antineoplastic composition comprising about 20 μM to about 80 μM of a compound selected from the group consisting of tetra-o-methyl nordihydroguaiaretic acid ($M_4N$) and maltose-$M_3N$;
and about 1 μM to about 10 μM of 7-hydroxystaurosporine.
2. A method of inhibiting tumor growth in an animal, said method comprising administering the synergistic antineoplastic composition of claim 1.
3. The method of claim 2 wherein the mammal is a human, cat, dog or mouse.
4. The method of claim 2, wherein the tumor is selected from the group consisting of breast cancer, prostate cancer, pancreatic cancer, colon cancer, hepatoma, glioblastoma and ovarian cancer.
5. A method of inhibiting tumor metastasis in a mammal, said method comprising administering the synergistic antineoplastic composition of claim 1.
6. The method of claim 5 wherein the mammal is a human, cat, dog or mouse.
7. The method of claim 5 wherein the tumor is selected from the group consisting of breast cancer, prostate cancer, lung cancer, colon cancer, ovarian cancer, brain cancer and pancreatic cancer.
8. A method of inhibiting caspase-dependent cell death in a subject afflicted with a disease or disorder, said method comprising the step of administering the synergistic antineoplastic composition of claim 1, to said subject.
9. The method of claim 8 wherein the disease or disorder is myocardial infarction.
10. The method of claim 8 wherein the disease or disorder is cancer.
11. The method of claim 10 wherein the caspase dependent cell death is caused by a chemotherapeutic agent.

* * * * *